US010239897B2

United States Patent
Pasqua et al.

(10) Patent No.: US 10,239,897 B2
(45) Date of Patent: Mar. 26, 2019

(54) BORTEZOMIB-BASED DELIVERY SYSTEM

(71) Applicant: NanoSiliCal Devices S.r.l., Rende (IT)

(72) Inventors: Luigi Pasqua, Rende (IT); Antonella Leggio, Rende (IT); Angelo Liguori, Rende (IT); Catia Morelli, Rende (IT); Sebastino Andò, Rende (IT)

(73) Assignee: NANOSILICAL DEVICES S.R.L., Rende CS (IT)

( * ) Notice: Subject to any disclaimer, the term of this patent is extended or adjusted under 35 U.S.C. 154(b) by 0 days.

(21) Appl. No.: 15/570,254

(22) PCT Filed: Apr. 29, 2016

(86) PCT No.: PCT/IT2016/000111
§ 371 (c)(1),
(2) Date: Oct. 27, 2017

(87) PCT Pub. No.: WO2016/174693
PCT Pub. Date: Nov. 3, 2016

(65) Prior Publication Data
US 2018/0127441 A1    May 10, 2018

(30) Foreign Application Priority Data

Apr. 29, 2015 (IT) .............................. RM2015A0184

(51) Int. Cl.
| | |
|---|---|
| *C07F 7/18* | (2006.01) |
| *A61K 47/69* | (2017.01) |
| *A61K 45/06* | (2006.01) |
| *A61P 35/00* | (2006.01) |
| *A61K 31/695* | (2006.01) |

(52) U.S. Cl.
CPC .......... *C07F 7/1804* (2013.01); *A61K 31/695* (2013.01); *A61K 45/06* (2013.01); *A61K 47/6923* (2017.08); *A61P 35/00* (2018.01)

(58) Field of Classification Search
CPC .. A61K 31/695; A61K 45/06; A61K 47/6923; A61P 35/00; C07F 7/1836
See application file for complete search history.

(56) References Cited

FOREIGN PATENT DOCUMENTS

| WO | 2014/170628 | 10/2014 | |
|---|---|---|---|
| WO | WO 2014/170628 | * 10/2014 | ............... C07F 5/02 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
International Search Report for PCT/IT2016/000111, dated Aug. 17, 2016, all pages.
Written Opinion of the ISA for PCT/IT2016/000111, dated Aug. 17, 2016, all pages.

* cited by examiner

*Primary Examiner* — Erich A Leeser
(74) *Attorney, Agent, or Firm* — Nixon & Vanderhye P.C.

(57) ABSTRACT

The invention relates to a class of molecules obtained for conjugating a species or substrate to Bortezomib by means of bonds of the boronic diester type which are stable in a neutral environment but which are capable of being degraded in a slightly acid environment (pH=4.5-5.0) releasing the drug Bortezomib and which can also be conjugated on the surface of a cro-nanosystem (a type of substrate) for the delivery of drugs in such a way as to become a constituent thereof. They represent a class of Bortezomib prodrugs with respect to hydrolysis of the boronic ester. They may be used in the transport and release of Bortezomib when it is necessary to diffuse it in slightly acid pH environments after passing through neutral pH environments in which the drug remains stably conjugated in the form of a non-biologically-active boronic ester. In practice the invention may be used for the intracellular release of Bortezomib where the latter will permit the drug to be transported in a biologically inactive form through the blood flow while undergoing pH-induced chemical degradation once introduced into the intracellular environment, inducing diffusion of the therapeutically effective form of Bortezomib. In the situation where this is used as a constituent of a drug delivery system, it will be anchored thereto and being provided with a delivery function it will be capable of reaching the intracellular environment at pH 4.5 where degradation of the prodrug to which the invention relates will take place, inducing diffusion of the Bortezomib.

20 Claims, 7 Drawing Sheets

BORTEZOMIB-BASED DELIVERY SYSTEM

This application is the U.S. national phase of International Application No. PCT/IT2016/000111, filed 29 Apr. 2016, which designated the U.S. and claims priority to Application No. IT RM2015A000184, filed 29 Apr. 2015; the entire contents of each of which are hereby incorporated by reference.

TECHNICAL FIELD OF THE INVENTION

This invention relates to a release system based on Bortezomib in the form of micro- or nanoparticles (or carrier) provided with drug delivery systems. The Bortezomib in the carrier may be in such form or in the form of a derivative, as is explained below.

More particularly the invention relates to a class of derivatives obtained by reacting a molecular unit (or linker) with Bortezomib through a link of the boronic diester type.

These derivatives are stable in a neutral environment but are capable of being degraded in a slightly acid environment (pH=4.5-5.0) releasing the drug Bortezomib, and they can also be conjugated with the carrier through the linker.

The derivatives according to the invention represent a class of Bortezomib prodrugs relating to hydrolysis of the boronic ester and may be used for the transport of Bortezomib and its release in slightly acid pH environments, such as the intracellular environment, after it has passed through media having a neutral pH (such as the blood flow) in which the drug remains stably conjugated in the form of a non-biologically-active boronic ester.

In practice the derivatives according to the invention may be used for the intracellular release of Bortezomib in that they allow the drug to be transported through the bloodstream, which is characterised by a pH which is approximately neutral (7.4), in a biologically inactive form, whereas once introduced into the intracellular environment, which is characterised by an acid pH (approximately 4.5-5.0), they undergo pH-induced chemical degradation, giving rise to diffusion of the therapeutically effective form of Bortezomib.

In the case where such derivatives are used as the constituents of a drug delivery release system they will be anchored thereto by means of a linker unit, and this (the Drug Delivery System), having a delivery function, will be capable of reaching the intracellular environment at a pH of 4.5-5.0, where degradation of the prodrug to which the invention relates will take place, giving rise to the diffusion of Bortezomib. For example the derivatives according to the invention may be used for the purpose of achieving the intracellular release (at pH 4.5-5.0) of Bortezomib following endovenous administration (in a neutral pH environment).

The derivatives according to the invention are used in the preparation of therapeutic systems capable of releasing Bortezomib in the intracellular environment.

PRIOR ART

Bortezomib [3-methyl-1-(3-phenyl-2-(pyrazine-2-carboxyamido)-propanamido) butyl boronic acid] is represented by formula (I), and has in its structure the boronic acid functional group, and as such has similar reactivity to boronic acids.

(I)

Bortezomib is a synthetic compound belonging to a class of new generation antineoplastic agents which act by inhibiting the chemotrypsin-like activity of proteasome 26S and consequently degrading cell proteins [Adams J, Palombella V J, Sausville E A, Johnson J, Destree A, Lazarus D D, Maas J, Pien C S, Prakash S, Elliott P J. Cancer Res (1999), 59:2615-2622; Pickart C M, Eddins M J. Biochim Biophys Acta. 2004 Nov. 29; 1695(1-3):55-72.]

This is used clinically for the treatment of first diagnosed or refractory multiple myeloma (MM) and other forms of tumour such as mantle cell lymphoma [Jagannath S, Barlogie B, Berenson J, Siegel D, Irwin D, Richardson P G, et al. Brit J Haematol (2004) 127: 165-172; Orlowski R Z. Exp Rev Anticancer Ther (2004) 4:171-179]. It has also been tested for the treatment of many solid tumours, such as tumours of the prostate, breast, lungs, kidneys and ovaries [Cusack J C. Cancer Treat Rev (2003) 29: 21-31]. Bortezomib inhibits the ubiquitin-proteasome pathway. This inhibition gives rise to numerous effects on tumour cells, including changes in cell proliferation [King R W, Deshaies R J, Peters J M, Kirschner M W. Science (1996) 274: 1652-1659], cell adhesion [Read M A, Neish A S, Luscinskas F W, Palombella V J, Maniatis T, Collins T. Immunity (1995) 2: 493-506] and angiogenesis [Dulic V, Kaufmann W K, Wilson S J, Tlsty T D, Lees E, Harper J W, et al. Cell (1994) 76:1013-1023] which bring about a stop to the cell cycle and apoptosis. These effects mainly apply to tumour cells, but may also affect normal cells [Adams J. Semin Oncol (2001), 28:613-619].

The main collateral effect caused by treatment with Bortezomib is a peripheral neuropathy which often represents the dose-limiting factor for its clinical use and may also result in treatment being discontinued. In particular Bortezomib-induced peripheral neuropathy takes the form of distal paraesthesia and neuropathic pain with a "glove and stocking" distribution [Cata J P, Weng H R, Burton A W, Villareal H, Giralt S, Dougherty P M. J Pain (2007) 8: 296-306; Cavaletti G, Pezzoni G, Pisano C, Oggioni N, Sala, F, Zoia C, Ferrarese C, Marmiroli P, Tredici G. Neurosci. Lett. (2002) 322:103-106; Richardson P G, Briemberg H, Jagannath S, Wen P Y, Barlogie B, Berenson J, et al. J Clin Oncol (2006) 24: 3113-3120; Meregalli C, Canta A, Carozzi V A, Chiorazzi A, Oggioni N, Gilardini A, Ceresa C, Avezza F, Crippa L, Marmiroli P, Cavaletti G. Eur J Pain. (2010) 14:343-350]. These symptoms arise during treatment with Bortezomib but are often also protracted after treatment has been interrupted, causing appreciable disabilities in patients with severe repercussions on their quality of life [Jagannath S, Barlogie B, Berenson J, Siegel D, Irwin D, Richardson P G, et al. Brit J Haematol (2004) 127: 165-172]. So far however it is still not clear what specific morphological changes in the peripheral nerve fibres are associated with the various painful components of Bortezomib-induced neuropathy.

Systems constructed using mesoporous silica particles which are potentially useful in the release/delivery of drugs or genes are described in the documents listed below: WO2007108016, WO201209448, US20090311332

Document WO2007108016 describes drug delivery micro- and nanosystems constructed using mesoporous silica particles and characterised by the presence of a receptor-specific ligand on the outer surface of the particle and a drug introduced into or predominantly bound within the pores. The receptor-specific ligand, the receptors of which are overexpressed in tumour cells, is recognised and internalised by the tumour cells and draws in with it all the nanosystem which releases the drug in the intracellular environment in response to specific stimuli. The receptor-specific ligand and the drug may be of different types. The aforesaid systems make possible effective targeted treatments with low drug doses and low toxicity and collateral effects.

Document WO201209448 describes submicron structures based on porous silica with surfaces coated with a cationic polymer. These can include an oligonucleotide and a therapeutic agent. The use of Bortezomib is cited among the therapeutic agents claimed, moreover the systems proposed do not provide for mechanisms for the release of pH-sensitive drugs.

Document US 200903110332 describes a method for synthesising mesoporous silica nanoparticles and their corresponding applications. The method includes separation of the particles on the basis of their size.

A material which is to be delivered is introduced into the particles produced and controlled release is achieved by reducing the pH at the surface of the mesoporous silica particle. Bortezomib or prodrugs of Bortezomib are not mentioned.

The object of this invention is to develop Bortezomib derivatives which permit more effective delivery with a reduction in collateral effects in comparison with Bortezomib as such when it is administered in accordance with the known art. In particular the object of the invention is to inhibit the peripheral neuropathies which originate as an adverse collateral effect associated with the administration of Bortezomib.

SUMMARY OF THE INVENTION

The object of the present invention thus resides in a release system comprising the carrier/linker/Bortezomib association as will shortly be defined.

Another object of the invention is a class of Bortezomib derivatives capable of releasing Bortezomib as a consequence of their degradation which takes place at a pH of 4.0-5.5, preferably pH 4.5-5.0.

These derivatives have general formula (II) which will shortly be described. They may be used as such for the same therapeutic uses as Bortezomib and can be introduced into known micro- and nanoparticle systems (such as for example described in WO2007108016) incorporating a ligand for delivery of the drugs.

The derivatives according to the invention make it possible to reduce the collateral effects normally associated with high doses of antitumour drugs which are necessary in conventional treatments as a result of direct administration to the tumour cells alone directly in an intracellular environment.

Yet another object of the invention is a conjugate comprising the Bortezomib derivatives defined above with micro- and nanoporous particles. Submicron particles based on silica having a morphology provided with cavities capable of receiving the therapeutic agent or agents or the prodrug which has to be delivered are preferred. Particularly preferred are the micro- and nanoparticles described in WO2007/108016.

Yet another object is pharmaceutical compositions comprising the prodrug or the delivery system for the treatment of tumour forms in general or to alleviate the collateral effects associated with the administration of Bortezomib.

Further objects of the invention will be apparent from the following detailed description.

DETAILED DESCRIPTION OF THE INVENTION

Figure 1:
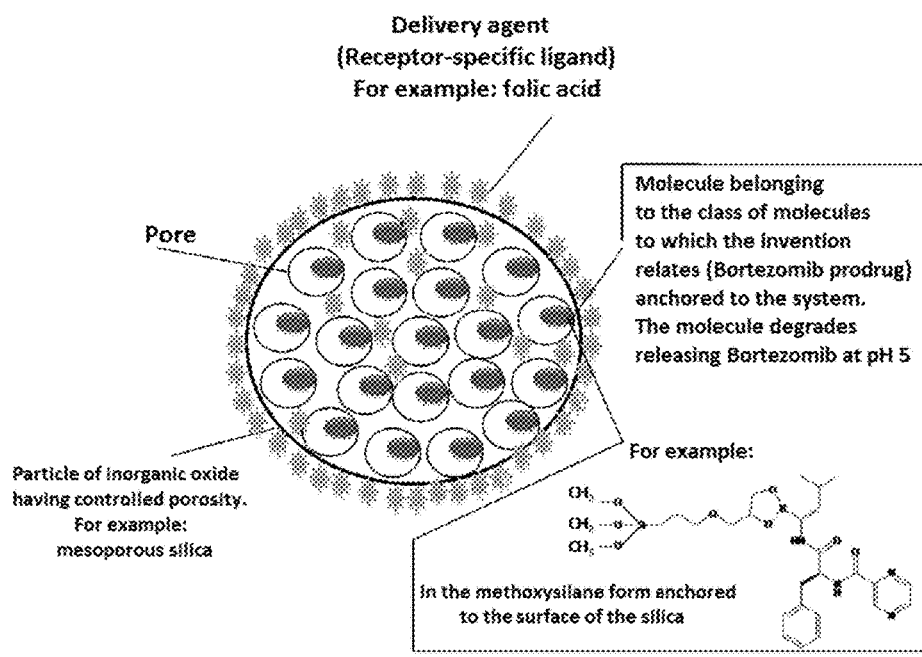
FIG. 1. Diagram of the conjugate comprising mesoporous silica coupled with folic acid on the outer surface and housing the Bortezomib derivative (shown diagrammatically as an oval) chemically anchored in the pores.
Figure 2:
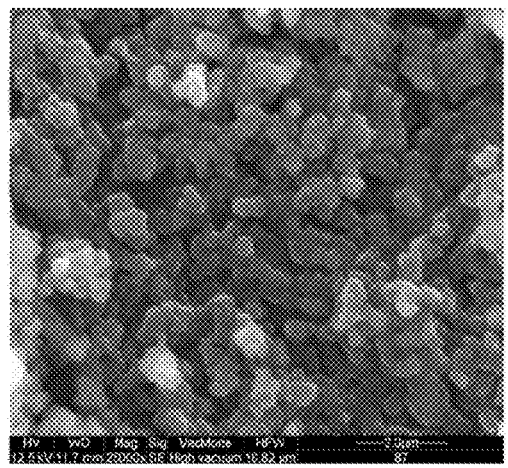
FIG. 2. A micrograph of a mesoporous silica of the MSU type obtained using a scanning electron microscope.

The following definitions apply in the context of this invention:
by drug delivery system is meant the Carrier/Linker/Bortezomib conjugate;

by prodrug of Bortezomib derivative is meant the compound of general formula (II) obtained by reaction between the linker and Bortezomib at the boronic acid functional group;

by linker or molecular unit or bidentate ligand is meant the molecule of general formula (III), one extremity of which is capable of reacting with the boronic acid functional group of Bortezomib and the other extremity capable of binding to the carrier;

by ligand or agent having a delivery function is meant a compound responsible for delivery and recognition of molecules abundantly expressed on the surface of tumour cells, thus bringing about selective delivery to the target tissue;

by carrier is meant a particle, for example a porous silica particle, having micro- to nanometric dimensions which can bind with the boron derivative of Bortezomib (the prodrug as defined above) on its surface, for example it may be a particle of porous silica or a matrix based on inorganic oxides having controlled porosity, which are for example obtained by "molecular imprinting" processes or through the use of surfactants (Katz, A.; Davis, M. E. *Molecular Imprinting of Bulk, Microporous Silica*, Nature, 2000, 403, 286-289);

by drug delivery micro- or nanosystem is meant a carrier as defined above which bears on its surface a compound designed to recognise molecules abundantly expressed on the surface of tumour cells, thus bringing about selective delivery to the target tissue, selected for example from: folic acid, biotin, peptides, antibodies, glycosides, carbohydrates or proteins, all compounds in themselves known.

The Bortezomib derivatives according to the invention are represented by general formula (II) and can be obtained by the chemical reaction of Bortezomib of general formula (I) with a bidentate ligand which can be represented by general formula (III) that reacts to form a cyclic boron derivative at the extremity of the ligand bearing R4.

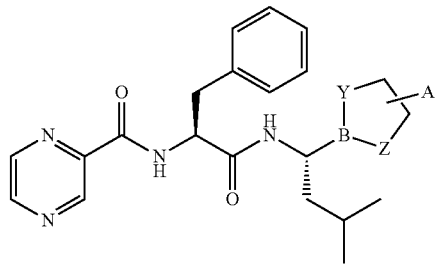

(II)

In the compound of formula (II) Y and Z represent, independently of each other, —NH, —O—, —S—, and A is the substituent obtained after the reaction between the compound of formula (I) (Bortezomib) and the compound of formula (III).

In particular A has the following meaning

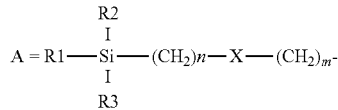

The bidentate ligands (or linkers) according to the invention are represented by general formula (III):

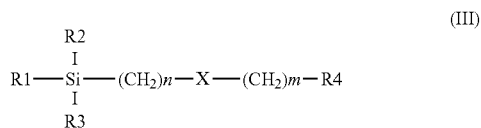

in which:

R1, R2, R3, independently of each other, are selected from $CH_3$, $C_2H_5$, $OCH_3$, $OC_2H_5$, $OC_3H_7$, $OC_4H_9$, $OC_5H_{11}$;

X is a single bond or S, O, NH;

R4 is selected from $NH_2$, SH, epoxide, halogen, CN, thiocyanate, —CH=$CH_2$;

n and m are positive integers such that n=0-5 and m=0-3 with n+m≥1

The Bortezomib derivatives allow it to be released at a pH of 4.5-5.0 by opening up the boron ring, while the other extremity can be left free or more advantageously linked to a known micro- or nanoparticle system.

The Bortezomib derivatives according to the invention may be obtained by a process providing for the following basic stages.

The Bortezomib derivatives according to the invention may be prepared by first reacting Bortezomib with the linker of formula (III), thus obtaining the compound of formula (II), which is then bound to the carrier. As an alternative the linker of formula (III) is reacted with the carrier through the R1, R2 and R3 substituents, and what is obtained is caused to react with Bortezomib, obtaining the Carrier/Linker/Bortezomib system according to the invention. All the reactions are organic reactions which fall within the scope of the knowledge of those skilled in the art. Typical reaction conditions are for example illustrated in the examples section.

The Bortezomib derivatives may be used for the intracellular release of Bortezomib in that they allow the drug to be transported in a biologically inactive form through the blood flow, but once they reach the intracellular environment they undergo chemical degradation induced by the characteristics of the environment (pH), releasing free Bortezomib.

When the derivative is used as a constituent of a drug delivery system it will be anchored thereto, and as the entire system has a delivery function it will be capable of reaching the intracellular environment at pH 4.5-5.0 where degradation of the prodrug will take place with the release of free Bortezomib.

The derivative is degraded, releasing the Bortezomib at a pH of 4.5-5.0 (the typical pH of the intracellular environment). For a general description of the micro-nanosystems presented here, where these are used for transport of the Bortezomib prodrugs that are the object of the invention, see document WO2007108016.

The diagram shown below describes the potential use of the invention described. In particular a potential use as a component of a micro- or nanosystem for the intracellular release of Bortezomib is illustrated. The system comprises a matrix based on inorganic oxides with regular and controlled porosity (in the particular case a particle of mesoporous silica is illustrated), characterised in that a substance responsible for delivery and molecular recognition (illustrated diagrammatically as an asterisk; by way of example folic acid has been selected in FIG. 1) is selectively coupled, preferably on the outer surface, and, preferentially in the pores, the molecule belonging to the class of molecules which are the object of the invention (prodrug of Bortezomib, represented diagrammatically as an oval), chemically anchored to the system.

In a further embodiment of the invention the inorganic matrix comprises, in addition to or as a replacement for the substances responsible for delivery and molecular recognition, other molecules having a marker function, in particular fluorescent markers. These molecules can be combined on the outer surface of the inorganic matrix in combination with the delivery substances. Rhodamine and fluorescein are preferred. A method of preparation is described in Morelli, C. et al. L. *PEG-templated mesoporous silica nanoparticles exclusively target cancer cells*. Nanoscale. 2011 August; 3(8):3198-207, where the preparation of mesoporous silicas bound to fluorescein and folic acid is described.

The Bortezomib derivatives according to the invention represent a class of Bortezomib prodrugs relating to hydrolysis of the boronic ester and can also be conjugated on the surface of a micro-nanosystem for drug delivery in such a way as to become a constituent thereof.

These are chemically stable at a neutral pH, while they decompose with the release of Bortezomib at slightly acid pH (4.5-5.0). They can be used in the transport and release of Bortezomib when it is necessary to induce its diffusion in environments having slightly acid pH after it has passed through media having a neutral pH in which the drug remains stably conjugated in the form of a non-biologically-active boron derivative.

These derivatives may also be bound to micro- and nanoparticle systems used for the transport of Bortezomib when it is necessary to induce its diffusion in environments having a slightly acid pH after it has passed through media having a neutral pH in which the drug remains stably conjugated in the form of a non-biologically-active boronic ester, conditions which occur if the abovementioned micro- and nanosystems for drug delivery are used for endovenous injection.

The Bortezomib derivative according to the invention has in its structure the boronic ester functional group and as such has reactivity similar to that of boronic esters.

The molecules (bidentate ligands) which have been caused to react with Bortezomib to give rise to prodrugs having the properties described above are illustrated by general formula (III).

A particularly preferred molecule is 3-glycidoxypropyl-trimethoxy-silane of formula 2.1:

2.1

Other particularly preferred molecules are:

3-aminopropyltriethoxysilane 3-aminopropyltrimethoxysilane 4-aminobutyl-dimethyl methoxysilane 3-(2-aminoethylamino)propyl-trimethoxysilane (N-[3-(trimethoxysilyl)propyl]ethylenediamine)

3-[2-(2 aminoethylamino) ethylamino]-propyltrimethoxysilane; $(CH_3O)_3Si(CH_2)_3NHCH_2CH_2NHCH_2CH_2NH_2$ 3-(2-aminoethylamino)propyl-methyldimethoxysilane 3-mercaptopropyltrimethoxysilane 3-glycidoxypropyldimethoxymethylsilane 3-glycidoxypropyldimethylethoxysilane 3-glycidoxypropyltrimethoxysilane

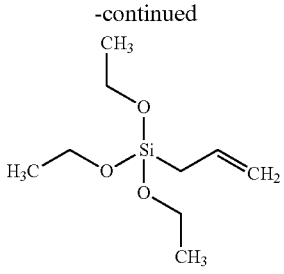

Allyltriethoxysilane

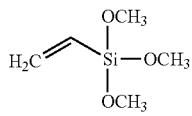

Allyltrimethoxysilane

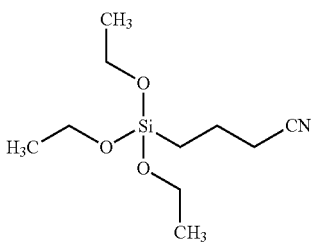

3-cyanopropyltriethoxysilane

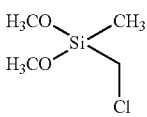

Chloromethyl(methyl)dimethoxysilane

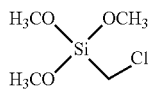

Chloromethyltrimethoxysilane

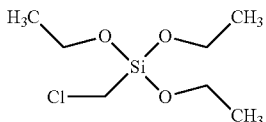

Chloromethyltriethoxysilane

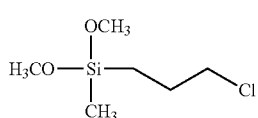

(3-chloropropyl)dimethoxymethylsilane

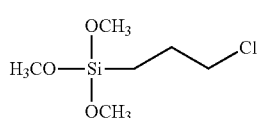

(3-chloropropyl)trimethoxysilane

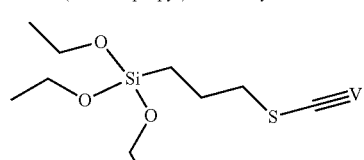

3-thiocyanatopropyltriethoxysilane

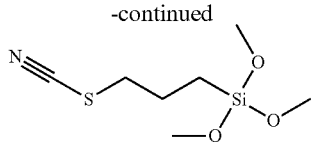

3-thiocyanatopropyltrimethoxysilane

Administration of Pharmaceutical Compositions

The present invention also includes pharmaceutical compositions comprising Bortezomib derivatives of formula (II) and Bortezomib-based conjugates, together with a pharmaceutically acceptable vehicle.

According to the present invention the derivatives and conjugates according to the invention may be formulated for single or contemporary, sequential or delayed administration with other active ingredients or prodrugs such as for example antitumour drugs, genetic material, radionucleides or fluorescent markers and may therefore be inserted in a single formulation or in separate formulations.

For use in the therapeutic field the pharmaceutical compositions are prepared in formulations suitable for the type of administration envisaged and the vehicles for the individuals requiring treatment, as known to those skilled in the art.

The formulation may for example be achieved through the use of salts and buffering substances or other excipients that are known to those skilled in the art and are pharmaceutically acceptable.

Administration of the derivatives and conjugates according to the invention may for example take place nasally, buccally, orally, intradermically, subcutaneously, intramuscularly, intraperitoneally, endovenously, intrathecally, intercranially, parenterally or intraperitoneally.

The pharmaceutical forms which can be used for injectables may for example include sterile aqueous solutions or dispersions, such as also sterile powders for the preparation of extemporary dispersions and all excipients, vehicles and buffers known to those skilled in the art for use in the preparation of injectables. The sterile powders are preferably prepared through desiccation techniques known to those skilled in the art, for example through desiccation under vacuum and freeze drying.

Therapeutically appropriate doses will be established by those skilled in the art responsible for treatment, on the basis of the severity of the conditions of the individuals requiring treatment and the selected administration route.

Any composition according to the invention may be included in an administration kit. By way of a non-limiting example, a kit according to the invention may comprise the Bortezomib derivative or the Carrier/Linker/Bortezomib delivery system formulated in an appropriate manner for specific administration, together with a pharmaceutically acceptable vehicle, for example water for injectable preparations or a pharmaceutically acceptable vehicle for oral administration, where applicable.

The components of the kit according to the invention may be in liquid form or lyophilised form and are preferably packed in suitable sterile containers, such as for example bottles, test tubes or syringes, either individually or already mixed.

The kits according to the invention may also include tools or devices for administration of the nanocarriers according to the invention via various possible administration routes, for example parenteral, intramuscular or endovenous administration.

The kits according to the invention also comprise instructions for use of the components and any other reagents not included in the kits themselves.

The delivery systems and prodrugs based on Bortezomib according to the invention are advantageously used in the treatment of tumours, in particular they are useful for alleviating collateral effects and improving the clinical conditions of individuals affected by forms of tumours, in particular carcinomas, multiple myeloma, lymphomas such as mantle cell lymphoma, tumours of the prostate, breast, lungs, kidneys and ovaries, more particularly carcinomas of the ovaries, kidneys, brain, lungs and breast.

The delivery systems and the prodrugs according to the invention can advantageously be used for all those diseases for which Bortezomib is used, in order to reduce its dose and to alleviate collateral effects, such as for example the morphological changes in peripheral nerve fibres, peripheral neuropathies, distal paraesthesias and neuropathic pain with a "glove and stocking" distribution.

The following examples, together with the figures, are provided purely by way of illustrating the invention and are not to be regarded as limiting its scope.

EXAMPLES

Binding of The Linker of Formula (iii) To the Nano Carrier and Subsequent Reaction with Bortezomib Synthesis of Silica Functionalised with 3-glycidoxypropyl

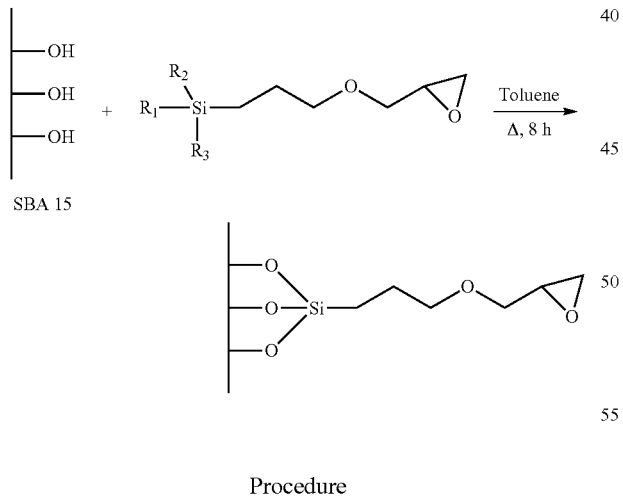

Procedure

The dried silica (SBA-15 0.55 g) is caused to react in an inert nitrogen atmosphere with 3-glycidoxypropylsilane (0.74 ml) in anhydrous toluene. The reaction was allowed to continue under reflux with magnetic stirring for eight hours. The functionalised silica was filtered off and washed with tetrahydrofuran on polyamide filters and subsequently dried. In this way silica functionalised with the glycidoxypropyl linker (1.1 g) was recovered.

[N-2(-aminoethyl)-3-aminopropylsilane)] (AEAPS)

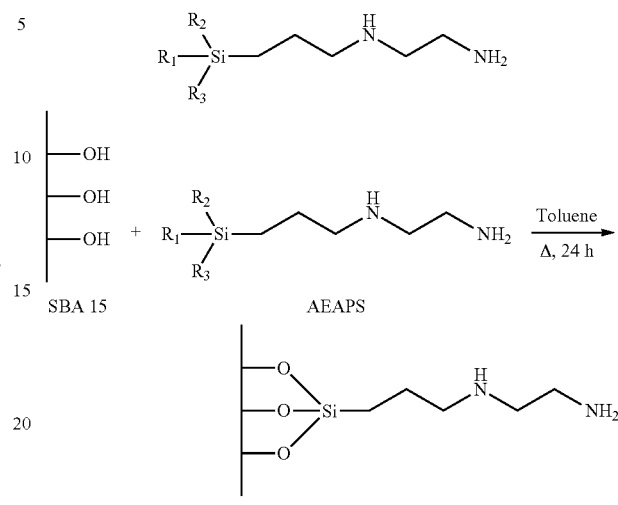

A (3-trimethoxysilylpropyl)diethylenetriamine (SiDETA)

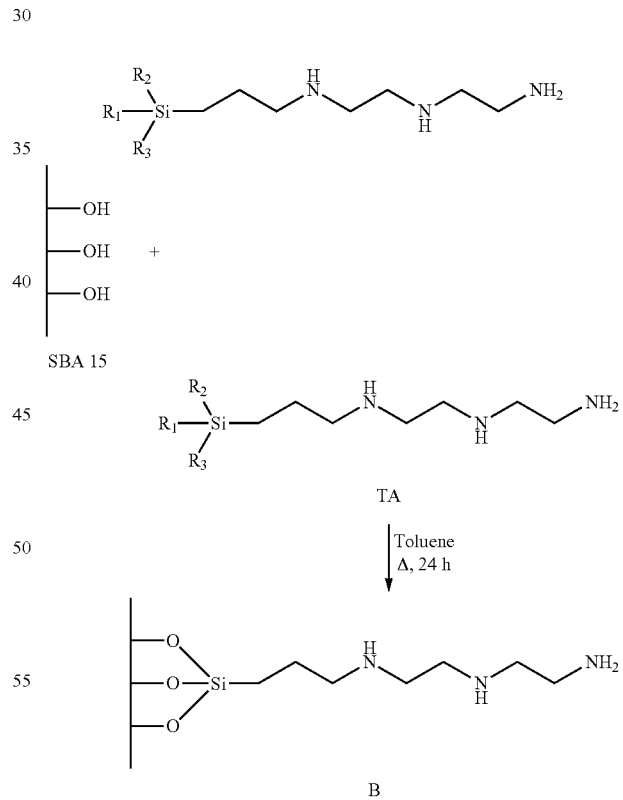

B

The mesoporous silica (SBA-15 or other type) was pre-activated at approximately 120° C. in a stove overnight, and was subsequently cooled and treated with aminosilane (AEAPS or SiDETA).

The mixture was heated with reflux with anhydrous toluene (30 ml/g of support) for 24 hours in a $N_2$ atmosphere. The reaction mixture was cooled to ambient temperature, the toluene and the excess diamine were removed by filtration under vacuum.

The recovered product was washed several times with dichloromethane and dried under vacuum at 40° C.

Alternative A

As an alternative the functionalisation reaction with 3-glycidoxypropyltrimethoxysilane may be carried out in dry dioxan.

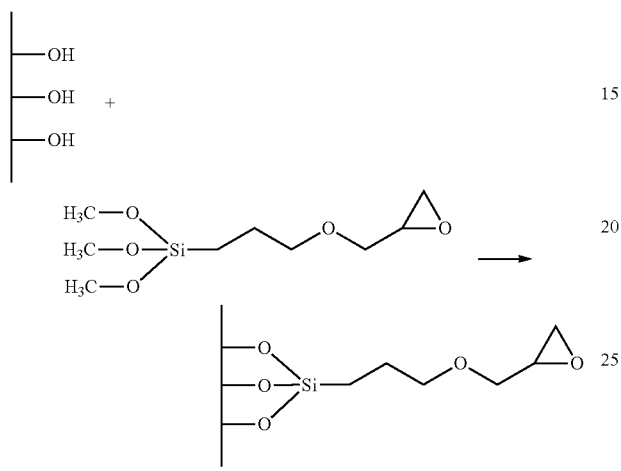

Grafting Reaction in Dry Dioxan for 18 Hours at Ambient Temperature

The process of synthesis provides for the suspension of 400 mg of mesoporous* material and the dissolution of 0.80 ml of 3-glycidoxypropyltrimethoxysilane in 12 ml of Dry Dioxan at ambient temperature. The mixture was left with magnetic stirring at ambient temperature for 18 hours. The mixture was subsequently filtered and washed in Dioxan and dry THF and dried at 45° C.

Alternative B

As an alternative this type of reaction may be carried out in ethanol at ambient temperature using longer reaction times.

In a typical preparation a solution obtained by dissolving 8.11 g of 3-aminopropyltriethoxysilane (APTES, $C_9H_{23}NO_3Si$) in 17.13 ml of ethanol was introduced into a suspension obtained by suspending 4 g of mesoporous silica of the MSU* type, suitably dried, in 14.3 ml of ethanol. The suspension obtained was stirred at ambient temperature for 18 hours, subsequently washed, filtered and dried.

*Any functionalisation procedure is valid for all types of mesoporous silica, however the alternatives proposed (above all alternative A which uses dioxan, which is a non-protic solvent) are suitable for the functionalisation of micro-nanosystems on which receptor-specific ligands such as folic acid or others have been previously bound, provided that it is carried out at ambient temperature and under reactivity conditions that preserve its biological activity.

3.50 g of product were recovered (it should be borne in mind that the following procedure may relate to both a material whose porosity was impregnated by the synthesis surfactant and a material without surfactant. In the above case material whose porosity was impregnated with the synthesis surfactant was used, and this if suspended in ethanol releases the surfactant or part thereof, rendering the data relating to the quantity of product recovered at the end of the yield calculation not very significant).

The above functionalisation reactions may be used for all linkers of general formula (III), varying the reaction time in relation to the degree of functionalisation desired.

Synthesis of Silica Functionalised with 3-Propoxypropyl-1,2-diol

Procedure

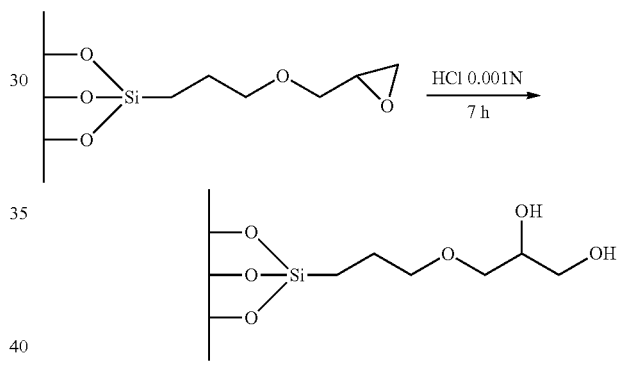

The silica functionalised with the glycidoxypropyl was caused to react with a 0.001N solution of HCl. The reaction was allowed to progress with magnetic stirring for seven hours at ambient temperature.

Filtration and washing with distilled water and analytical grade acetone on polyamide filters was performed. Silica functionalised with the diol functional group was recovered.

Anchoring of Bortezomib to the functionalised silica

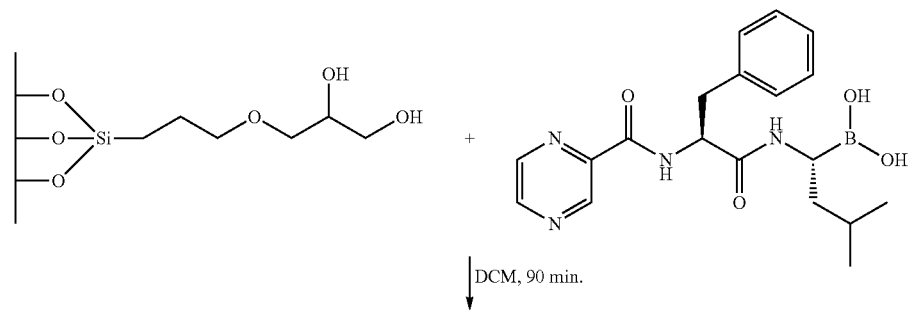

-continued

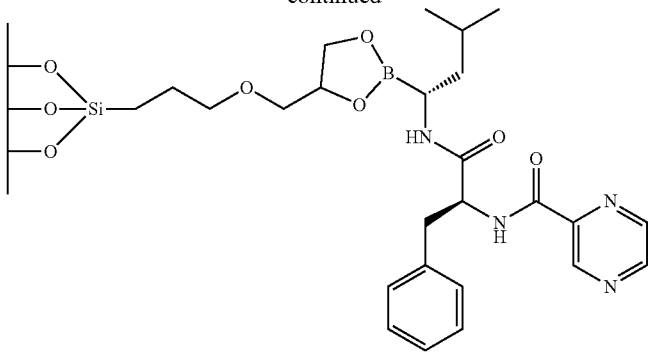

In an inert nitrogen atmosphere Bortezomib was caused to react with silica functionalised with the diol functional group in anhydrous dichloromethane. The reaction was allowed to proceed with magnetic stirring for ninety minutes.

Filtration and several washes were performed on polyamide filters using anhydrous dichloromethane. The silica with the Bortezomib bound as a cyclic boronic ester was recovered.

As an alternative the following preparation

Equimolar quantities of Bortezomib and functional group on the mesoporous silica (SBA-15 or other type) functionalised with AEAPS and SiDETA ligands were heated to 40° C. in anhydrous toluene in the presence of molecular sieves for 7 hours. The product recovered (diazaborolidine) was washed several times with dichloromethane and dried under vacuum.

Diazaborolidines hydrolyse rapidly in dilute acid solutions, but in neutral solutions hydrolysis is very slow (*J. Am. Chem. Soc.,* 1958, 80 (20), pp 5411-5413)

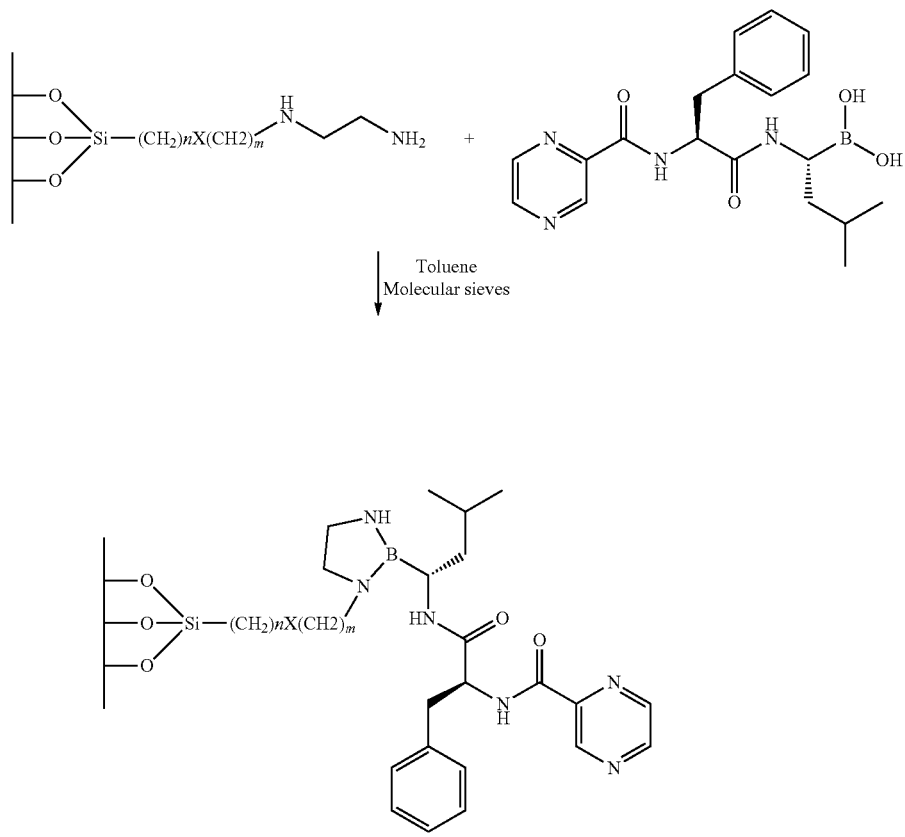

Preparation of the Bortezomib Derivative of Formula (II) and Subsequent Binding with the Nanocarrier
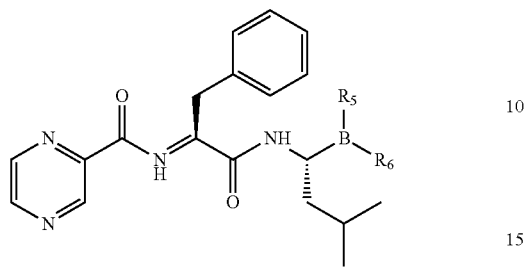
Compound II
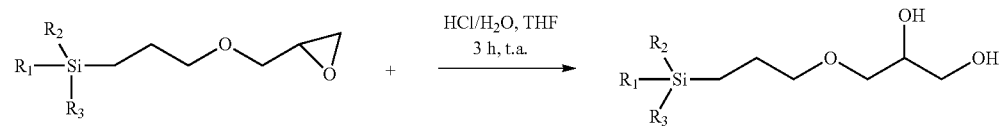
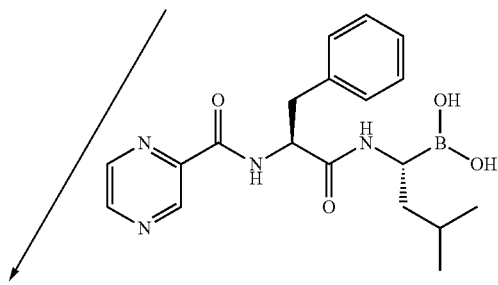
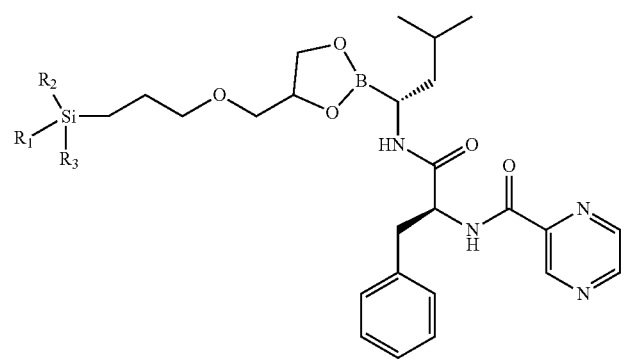

-continued

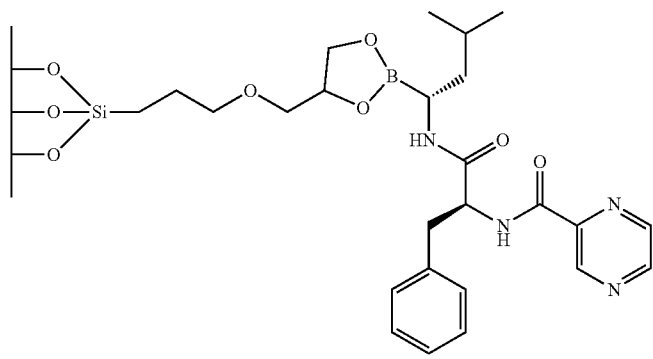

The 3-glycidoxypropylsilane was caused to react with a 0.001N solution of HCl in THF (tetrahydrofuran).

The reaction mixture was left for 3 hours with magnetic stirring.

The impure product was recovered by removing the solvent under reduced pressure conditions and was then treated with water and subsequently extracted with dichloromethane. The 3-(silylpropoxy)propane-1,2-diol was recovered in this way and then caused to react with Bortezomib in dichloromethane for approximately 2 hours. The boronic ester obtained was treated with silica (SBA-15 or other type) in ethanol for 48 hours at ambient temperature.

It was filtered and washed several times on polyamide filters using ethanol and anhydrous dichloromethane. Silica with the Bortezomib bound as a cyclic boronic ester was recovered.

Using the AEAPS and SiDETA ligands the link to Bortezomib can be made using the same conditions as are used for binding Bortezomib to silica functionalised with AEAPS and SiDETA. The derivative of formula (II) obtained can be then linked to the silica as the derivative of formula (II) obtained with the glycidoxy.

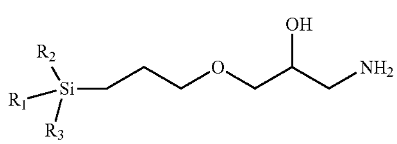

1-amino-3-(3-silyl)propoxy)propan-2-ol

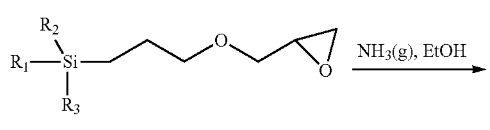

-continued

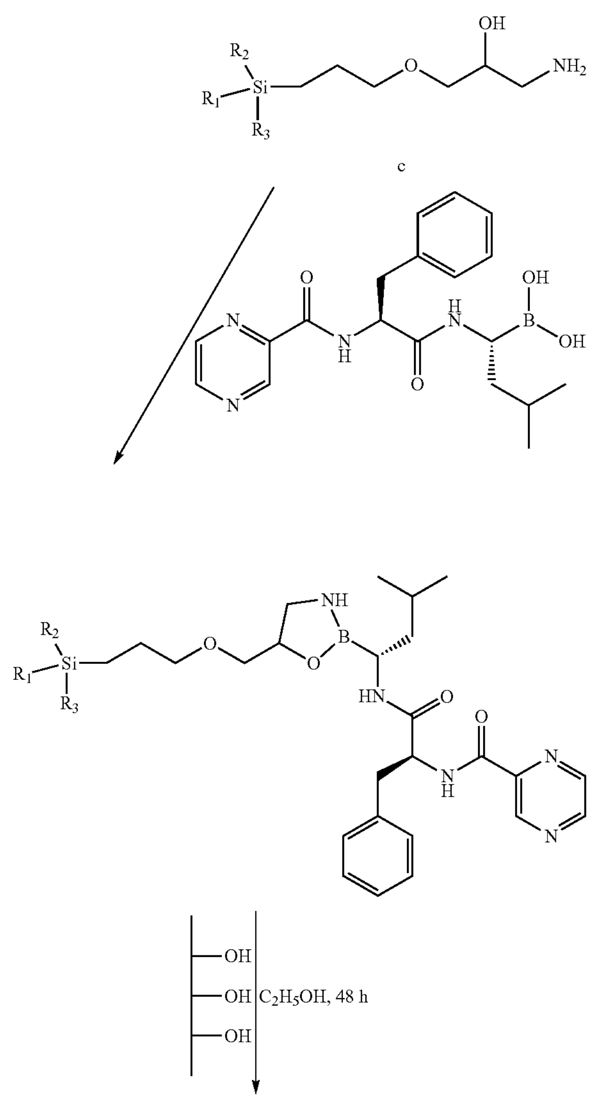

-continued

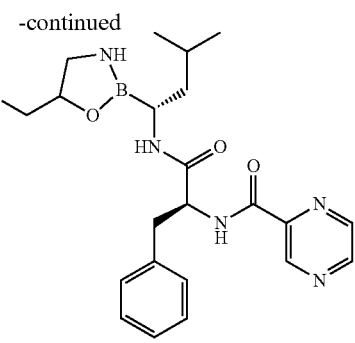

Gaseous ammonia at ambient temperature was caused to bubble through a solution of 3-glycidoxypropylsilane in ethanol for 10 hours. The solvent was removed under reduced pressure conditions and the 1-amino-3-[(3-silyl)propoxy]-propan-2-ol (C) was recovered and then subsequently treated with Bortezomib in equimolar quantities in toluene at 40° C. in the presence of molecular sieves.

The oxaazaborolidine obtained was treated with silica (SBA-15 or other type) in ethanol for 48 hours at ambient temperature.

This was filtered and washed several times on polyamide filters using ethanol and anhydrous dichloromethane. In the product recovered the Bortezomib was bound to the silica by means of a cyclic oxaazaborolidine structure.

With regard to the ligands of general formula (III) in which R4 is a double bond (allyltriethoxysilane, allyltrimethoxysilane, etc.), the double bond can be converted into an epoxide through an epoxidation reaction with peracids or through the formation of halohydrin and subsequent intramolecular nucleophilic substitution. The epoxide obtained was then processed in the same way as the glycidoxypropyl.

In the case where R4 is a halogen ((3-chloro-propyl)trimethoxysilane), the ligand may be converted into the corresponding alkene through a dehydrohalogenation (β-elimination) reaction and subsequently processed in the same way as the derivatives in which R4 is a double bond.

Synthesis of the Boronic Ester

Bortezomib can react with the diols obtained by opening the epoxy group present in the molecule, forming a cyclic boronic ester.

Preliminary experiments were performed using boronic acid models with a view to studying and developing the optimum reaction conditions for the formation of boronic esters starting from 3-glycidoxypropyltrimethoxysilane. 3-methylbutylboronic acid and phenylboronic acid were used as model substrates for this purpose.

The presence of trimethoxysilyl groups makes it possible to bind with the surface of the mesoporous silica. The ester bond formed can be hydrolysed in a slightly acid environment (pH 4.5-5.0) and allows the drug to be released at the endosomes and therefore at the target site limiting release away from the cell environment.

Nanoparticles Functionalised with the Boron Derivative in the Previous Example

Functionalisation

Bortezomib prodrugs can be used as the constituents of micro or nanosystems for drug delivery.

The experimental approach followed provided for functionalisation of the mesoporous silica nanoparticles and subsequent conjugation with the functionality introduced by the boronic acid. The mesoporous material was functionalised using 3-glycidoxypropyltrimethoxysilane; the epoxide functional group was subsequently hydrolysed to enable the Bortezomib to be anchored.

The 3-glycidoxypropyltrimethoxysilane molecule is capable of binding the Bortezomib and at the same time can be anchored to the surface of the mesoporous silica.

The mesoporous material of the SBA-15 type was synthesised by modifying a preparation reported in the literature (Colloids and Surfaces A: Physicochem. Eng Aspects 229 (2003)1-8). The preparations used resulted from scaling-up of the original procedure and modifying it with regard to the EtOH/$H_2O$ molar ratio. Preparation of the SBA 15 sample: 4.2 g of Pluronic P-123 (Sigma Aldrich) and subsequently 0.7 g of CTAB (Alfa Aesar) were dissolved in a solution comprising 56.6 mL of ultrapure $H_2O$, 35 mL of 99+% EtOH (Sigma Aldrich) and 84 mL of 2M HCl. When dissolution was complete, 14 mL of TEOS (Sigma Aldrich) were added, the mixture obtained was left with stirring at ambient temperature for 30 minutes and subsequently transferred into a Teflon autoclave where it was allowed to age for 5 hours at 80° C. and subsequently at a temperature of 120° C. for 12 hours. The white precipitate obtained was recovered by filtration using polyamide filters with a porosity of 0.2 μm.

Alternatively mesoporous silicas of the MSU type obtained by the following synthesis protocol or similar (deriving from the procedures claimed in WO2007108016) may be used: a solution comprising 150 g of distilled $H_2O$ and 13.80 g of Triton X-100 (Sigma-Aldrich) was prepared in a 500 ml plastic beaker. Once the surfactant had been completely dissolved, a solution comprising 10 g of n-decane (99+% $C_{10}H_{22}$, Carlo Erba) and 14.50 g of TEOS ($Si(OC_2H_5)_4$, Sigma-Aldrich) was prepared. The solution was slowly poured along the walls of the beaker in which the surfactant-template was dissolved with very gentle stirring. The two-phase emulsion obtained was allowed to age with gentle stirring at ambient temperature for 8 days. Once the overlying organic phase had been removed, the emulsion was filtered using polyamide filters having a porosity of 0.2 μm.

Other types of mesoporous silica may be used as an alternative.

The SBA-15 mesoporous material was treated with 3-glycidoxypropyltrimethoxysilane (5) in anhydrous toluene under reflux for 8 hours (Diagram 1.1).[i]

Diagram 1.1

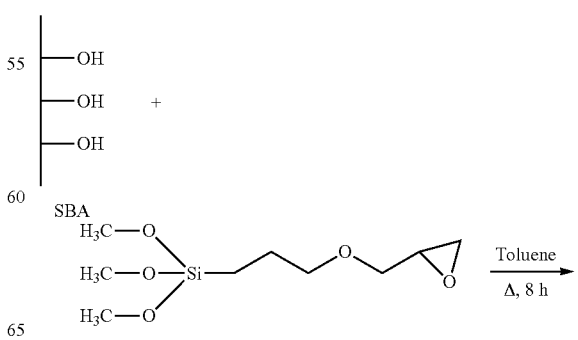

5

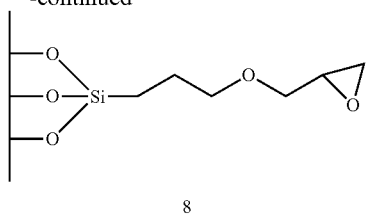

8

After filtering and washing with tetrahydrofuran the functionalised mesoporous silica was recovered and characterised by infrared (IR) spectroscopy, thermogravimetric analyses (TGA) and differential calorimetry (DSC).

A strong reduction in absorption at 3450 cm$^{-1}$ associated with stretching of the O—H bond in the silanol groups of the silica and the presence of stretching bands of C—H bonds at 2951 and 2853 cm$^{-1}$ corresponding to the chain of carbon atoms of the glycidoxypropyl group which were instead absent in the IR spectrum of the non-functionalised material were obtained in the IR spectrum.

Characteristics of the organic ligand are also the bands at 910 and 816 cm$^{-1}$ relating to asymmetric stretching of the epoxy ring.

The DSC and TGA analyses were performed on the SBA-15 mesoporous material after calcination and on material (8) functionalised with 3-glycidoxypropyl.

Considerable difference was found from the graphs (not shown) relating to the DSC and TGA analyses of the two samples. In the case of the functionalised material the TGA curve showed a loss of weight of approximately 11.3% (expressed in terms of the organic mass/(SiO$_2$+organic) mass ratio of 0.113). In the DSC curve the exothermic peak at a temperature of 248° C. was evidence of the combustion reaction of the glycidoxypropyl group.

In order to synthesise the boronic esters from the functionalised mesoporous silica (8) the epoxy ring was converted into the corresponding diol by hydrolysis in an acid environment.

Diagram 2.1

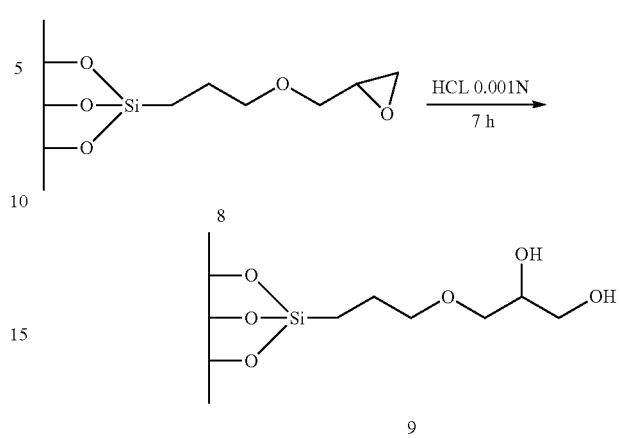

The hydrolysis reaction was carried out by treating mesoporous silica 8 with an aqueous solution of 0.001N hydrochloric acid for 7 hours at ambient temperature (Diagram 2.1).

Hydrolysed product 9 recovered by filtration was dried and characterised by IR spectroscopy and DSC and TGA analyses. An increase intensity in the band relating to stretching of the O—H bond at approximately 3443 cm$^{-1}$ attributable to the presence of the diol functional group and disappearance of the band at 910 cm$^{-1}$ corresponding to asymmetrical stretching of the epoxy ring were seen in the IR spectrum of product 9.

Experiments were performed on the formation of boronic esters starting from functionalised mesoporous silica 9 using 3-methylbutylboronic acid (6) as the model substrate. Compound 9 was treated with boronic acid 6 (Bortezomib analogue. Molecules similar to Bortezomib were used to link the reactivity of the molecule more directly with the structure of the functional group in support of the study to render it more rigorous, conditions similar to those in which the Bortezomib reaction takes place) in anhydrous toluene under reflux for 24 hours (Diagram 3.1).

Diagram 3.1

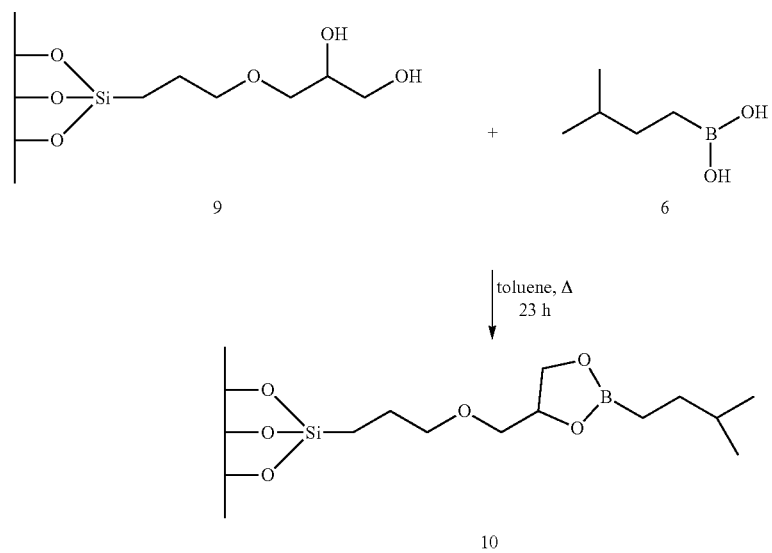

The product (10) recovered by filtration of the reaction mixture was washed with THF, in which solvent 3-methyl-butylboronic acid is soluble, dried and characterised by IR spectroscopy and DSC and TGA analyses.

Formation of the Boronic Diester

The boronic diester was formed using another model system: phenylboronic acid (an analogue of Bortezomib).

The reaction of 9 with phenylboronic acid was carried out under different conditions: reaction was carried out at ambient temperature for shorter times using dichloromethane as solvent. Mesoporous material 9 was treated with phenylboronic acid (11) in anhydrous dichloromethane at ambient temperature for 90 minutes (Diagram 4.1).

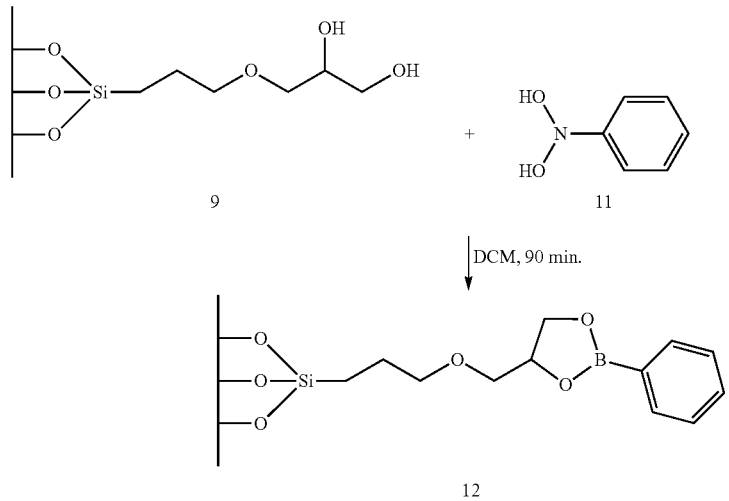

Diagram 4.1

Characterisation of product 12, recovered after filtration and washing with dichloromethane, using IR spectroscopy and DSC and TGA analyses, confirmed formation of the boronate. The IR spectrum showed, as characteristics of the structure of 12, a band corresponding to the stretching of aromatic C—H bonds at 3015 $cm^{-1}$ corresponding to the phenyl boronate, an absorption band at 1368 $cm^{-1}$ attributed to asymmetric vibration of the B—O bond of the boronate and two bands at 804 and 707 $cm^{-1}$ relating to folding perpendicular to the plane of the Ar—H bonds.

Bortezomib was then anchored to the SBA-15 mesoporous silica using conditions similar to those in the experiments with phenyl boronic acid (Diagram 5.1).

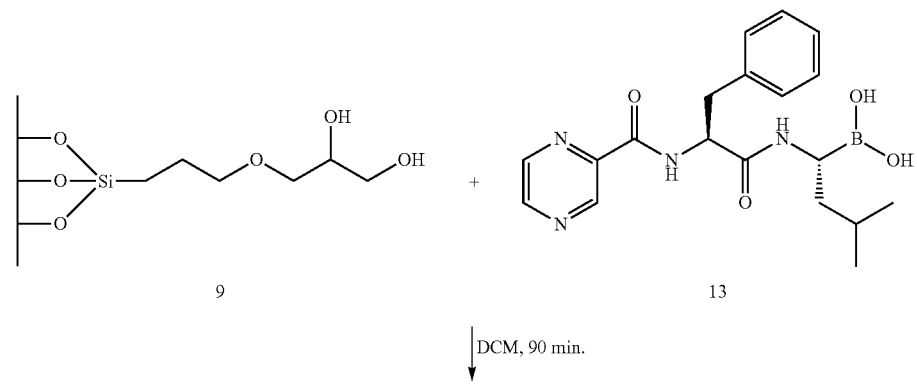

Diagram 5.1

-continued

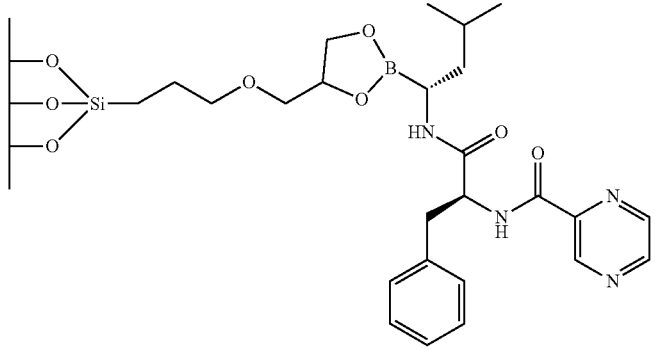

14

Analysis of the recovered product (14) by IR spectroscopy revealed the presence of a band corresponding to stretching of the amide bond present in the Bortezomib molecule at 1680 cm$^{-1}$ and a band at 1533 cm$^{-1}$ which could be attributed to folding of the NH group. Also typical of the Bortezomib molecule are the bands at 1446 cm$^{-1}$ relating to stretching of the C—N bond and at 744 and 701 cm$^{-1}$ corresponding to bending outside the plane of the aromatic ring. These bands were absent in the IR spectrum of the starting diol (9).

Anchoring of the Bortezomib to functionalised mesoporous material 9 was also confirmed by NMR analysis of compound 14 in the solid state.

Figure 3:
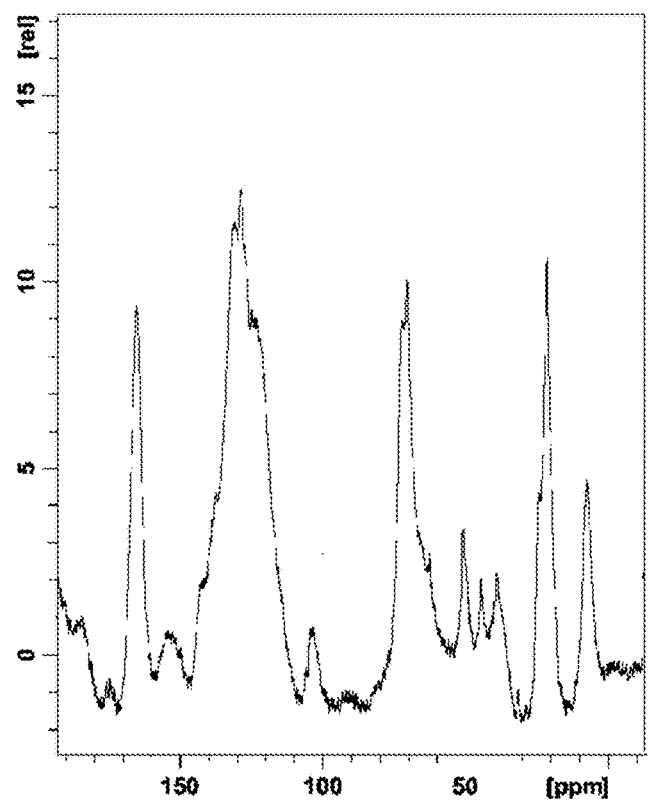
FIG. 3. $^{13}$C-NMR spectrum of the boronic ester.

All the signals attributable to both the organic ligand and the Bortezomib molecule were observed in the $^{13}$C-NMR spectrum of 14 (FIG. 3).

The signal at 7.52 ppm was due to the carbonium of the methylene group bound to the silica (Si—CH$_2$), while the two signals at 21.49 and 23.50 corresponded respectively to the methyls in the side chain of the amino acid residue of leucine and the central methylene carbon of the propyl chain bound to the silicon.

Signals relating to the carbon atoms of the two CH$_2$ groups bound to the ether oxygen atom of the organic linker (CH$_2$—O—CH$_2$) were also present at 70.50 and 71.56 ppm. Within the range 122.56-154.76 ppm the spectrum showed signals relating to the aromatic carbons of the Bortezomib molecule, and signals which can be attributed to the amide carbonyls of that molecule between 162.76 and 171.45 ppm.

In the $^{29}$Si-NMR spectrum in the solid state (not shown) two very strong peaks are observed at −110.6 and −105.5 ppm corresponding to the structures Q$^4$[Si(OSi)$_4$] and Q$^3$[Si(OSi)$_3$OH] respectively. Two peaks were also present in lower fields, −66.2 and −56.1 ppm, which can be attributed to the silicon of the T$^3$[RSi(OSi)$_3$] and T$^2$[RSi(OSi)$_2$OH] structures. The presence of the T species in the spectrum confirms that the organic ligand has attached to the inorganic structure of the silica. $^{11}$B-NMR analysis of 14 also shows signals which can be attributed to tricoordinated and tetracoordinated boron.

Bortezomib Prodrugs as Constituents of Drug Delivery Micro- or Nanosystems: Evaluation of the Stability of the Prodrug at Different pH The linker agent for anchoring the drug to the matrix, as shown above, is 3-glycidoxypropyltrimethoxysilane, which is capable of reacting with the boronic acid functional group of the drug and the mesoporous material at the same time.

According to this approach the drug is covalently bounded on the surface of the silica of a mesoporous material. The bond is stable at neutral pH and becomes labile at the slightly acid pH (4.5-5.0) which are typically found in the cell within endosomes and lysosomes.

These characteristics (together with the possibility of conjugating a receptor-specific ligand with the system) rendered the system as a whole potentially capable of diffusing within the circulatory flow (without significant losses of Bortezomib), being recognised and internalised by the tumour cells which overexpress the receptor-specific ligand receptors, with release of the drug following acid hydrolysis of the covalent bond.

The behaviour of the aforesaid system was evaluated by HPLC (High Performance Liquid Chromatography) in buffer solutions at pH 5.0 and pH 7.0 which mimic the intracellular and blood flow environments respectively.

Release of Bortezomib by the Drug Delivery System Comprising a Bortezomib Pre-Drug (Silica (SBA-15)/Linker/Bortezomib Conjugate).

The release profile of the drug from the overall system was studied by reproducing the physiological environments with which it would come into contact "in vitro". Release was therefore simulated in a solution at neutral pH (SBF) in order to simulate the route followed by the matrix-drug system within the circulatory flow up to its entry into the target cell, and in an acid solution at pH=5, which mimics the environment present in the endosomes, intracellular vesicles which form after the drug-matrix system has been internalised by endocytosis.

Preparation of c-SBF (Simulated Body Fluid)

The c-SBF are solutions buffered to different pH values which mimic the body fluid environment.

In particular there were used:

1) a buffer solution at pH 7, formed instead by potassium dihydrogen phosphate (KH$_2$PO$_4$) and sodium hydroxide (NaOH) reproducing the neutral environment of blood plasma.

2) a buffer solution of pH 4.4 based on sodium acetate and acetic acid, which reproduces the acid environment of the lysosomes with which the drug comes into contact after endocytosis.

Analytical Conditions for HPLC (High Performance Liquid Chromatography).

The release profile of the drug was evaluated by HPLC using acetonitrile/water (30/70 v/v) with 0.1% of formic acid as the eluent phase and a flow rate of 1.0 ml/min. The UV detector was set at 270 nm.

A Lichrosorb RP18 TEKNOKROMA 10 μm 25×0.46 column was used.

The volume of the injected solutions was 1 microliter and samples from the solution under physiological conditions were obtained at intervals of 30 minutes over 12 hours.

The calibration lines were drawn using three buffer solutions having different concentrations of Bortezomib. The drug showed three different peaks at pH 5 in the HPLC chromatogram.

The second and third peaks were considered for the purposes of evaluating drug release because the area which these subtend is linearly correlated with the concentration of the standard solutions.

Figure 4:
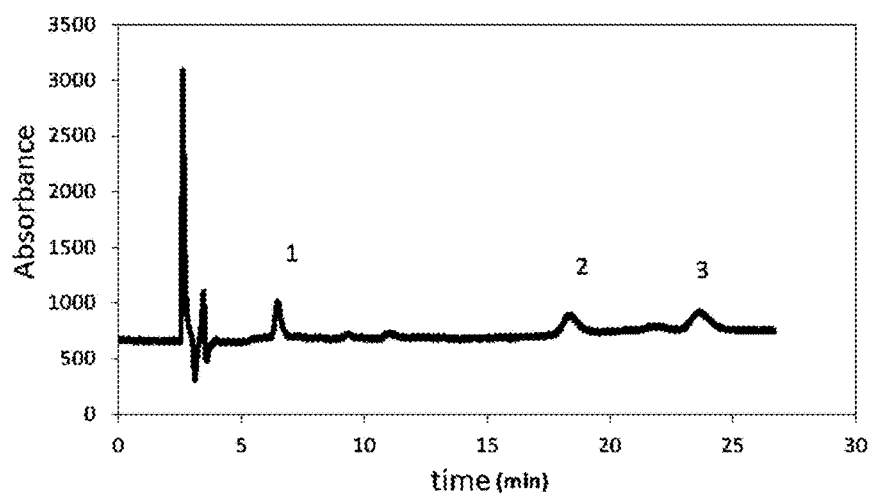
FIG. 4. Chromatogram of Bortezomib in a concentration of 70 ppm in simulated body fluid at a pH of 5.

The presence of two different peaks is due to the existence of two forms of Bortezomib at the pH in question which have different elution times as shown in FIG. 4.

Figure 5:
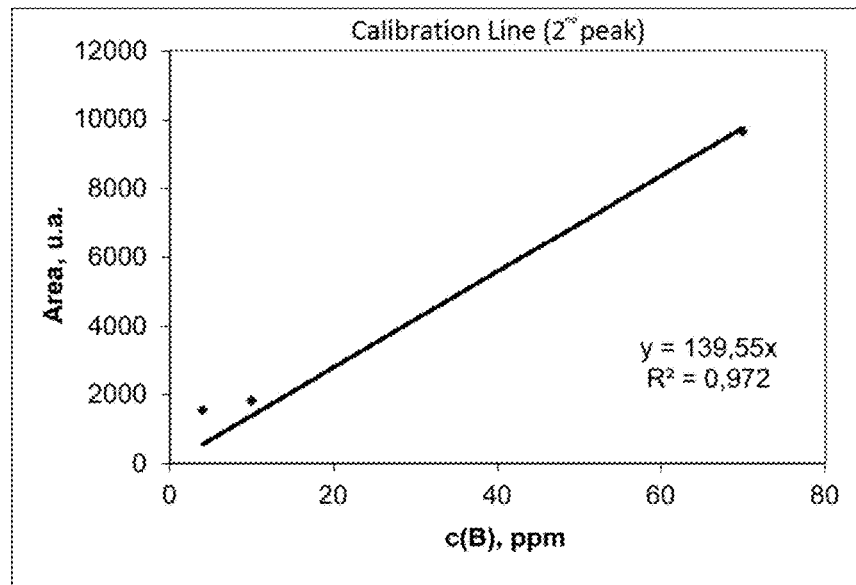
FIG. 5. Calibration line relating to the second peak in the chromatogram of the solution at pH 5.
Figure 6:
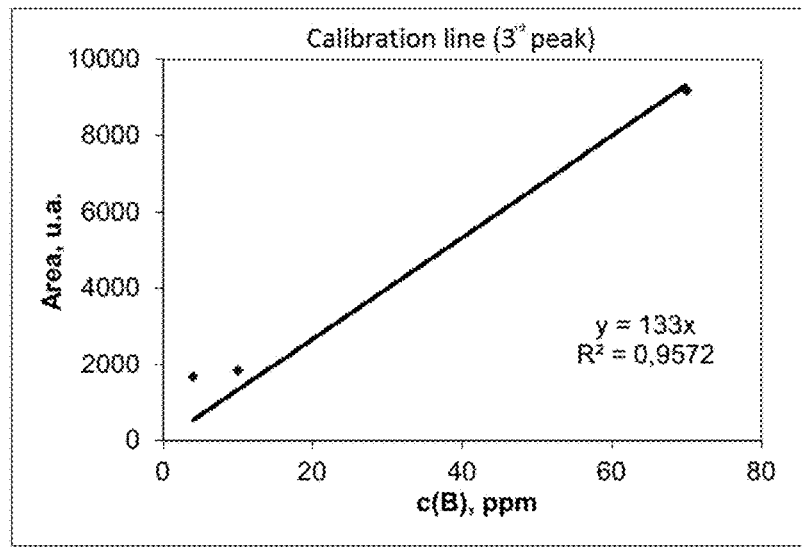
FIG. 6. Calibration line relating to the third peak of the chromatogram of the solution at pH 5.

The values obtained from analysis of the Bortezomib solutions at different concentrations are shown in Tables 1.1 and 2.1 for the peaks identified by the numbers 2 and 3 respectively in the chromatogram obtained at pH 5, shown in FIG. 4. The calibration lines obtained from peaks 2 and 3 are shown in FIGS. 5 and 6 respectively.

TABLE 1.1

| Values of the area subtended by the second peak for the solution at pH 5 | |
|---|---|
| Concentration (ppm) | Peak area (μa) |
| 4 | 1550 |
| 10 | 1829 |
| 70 | 9650 |

TABLE 2.1

| Values of the area subtended by the third peak for the solution at pH 5 | |
|---|---|
| Concentration (ppm) | Peak area (μa) |
| 4 | 1674 |
| 10 | 1830 |
| 70 | 9173 |

Release of Bortezomib in an Acid Environment (Buffer at pH=5)

The prodrug to which the invention relates (Silica (SBA-15)/linker/Bortezomib conjugate) as such or as a constituent of a drug delivery micro- or nanosystem (in this case the carrier in FIG. 1) is a molecule capable of releasing the active form of Bortezomib in slightly acid pH. Slightly acid pH are characteristic of the intracellular environment so the drug can diffuse within the cell environment if this is the first slightly acid pH compartment that the prodrug or the system of which it is a constituent comes into contact following internalisation by endocytosis after passing through the blood fluid at neutral pH. The endosomes (intracellular organelles) are in fact characterised by a slightly acid pH close to the value of 5, so release of the silica (SBA-15)/linker/Bortezomib conjugate sample was evaluated in a solution reproducing the endosome acid environment. An acetic acid/sodium acetate buffer, prepared by mixing 51 ml of an aqueous solution of 0.2M acetic acid obtained from 99% acetic acid (Carlo Erba) and 49 ml of a 0.2M aqueous solution of sodium acetate was used for this purpose. The latter was obtained by adding 0.803 g of sodium acetate [$CH_3COONa$] (Sigma Aldrich) to 49 ml of ultrapure $H_2O$.

The sample injected into the chromatography column was prepared by dissolving 4 mg of SBA-BORT material in 15 ml of buffer solution at a pH close to the value of 5 and stirred at a temperature of 37° C. to provide the best reproduction of the physiological conditions of the intracellular environment.

Table 3.1 shows the concentrations of Bortezomib found by HPLC in the buffer solution at pH 5, the relative areas of the peaks considered and the quantities expressed in grams at different time intervals.

Figure 7:
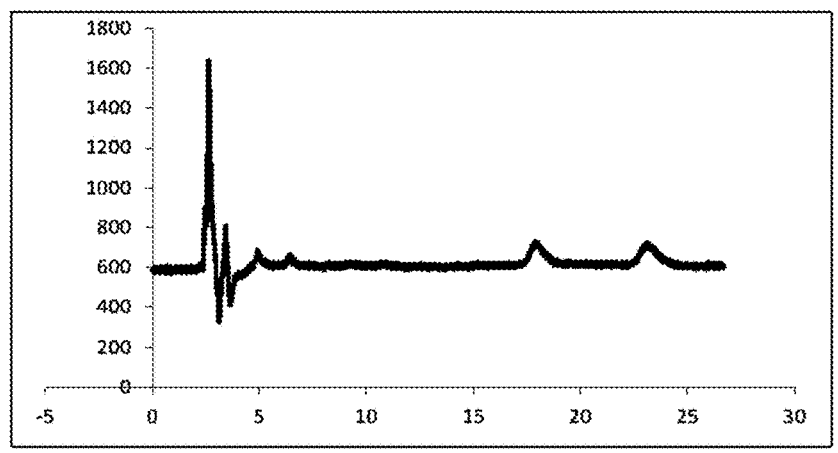
FIG. 7. Chromatogram of the SBA-BORT sample during the release tests in simulated body fluid at pH 5.

FIG. 7 shows an HPLC chromatogram during the release tests performed in simulated body fluid at pH 5.

The concentrations of the drug at different time intervals were obtained by dividing the value of each area subtended by the corresponding peak by the value of the gradient (y) of the calibration line.

In particular the concentrations found during the first 2.5 hours derive exclusively from the areas subtended by the second peak because the third was only detectable from the third hour onwards. Both peaks were however considered at subsequent times in order to obtain the final quantity of drug from the sum of the concentrations corresponding to all the individual areas.

As may be seen from the values shown in Table 3.1, the concentrations of the drug tend to increase progressively over time until approximately the eighth hour, and then come approximately constant values.

Release of Bortezomib in Neutral Environment (Buffer at pH=7).

In order to demonstrate the stability of the system within a neutral pH environment such as the blood flow, release tests were carried out on the SBA-BORT sample in a medium buffered at pH 7 at a temperature of 37° C. simulating the blood flow.

A $KH_2PO_4$/NaOH (potassium dihydrogen phosphate/sodium hydroxide) buffer was used for this purpose, prepared by dissolving 6.81 g of potassium dihydrogen phosphate in 291 ml of 0.10M sodium hydroxide.

TABLE 3.1

| Data relating to the release of SBA-BORT at pH = 5 as a function of time | | | | |
|---|---|---|---|---|
| Time (hours) | Area (μa) 2nd peak | Area (μa) 3rd peak | BORT concentration found (ppm) | Quantity of BORTEZOMIB released by 4 mg of matrix |
| 1 | 6798 | // | 48.71 | 0.04871 mg |
| 2 | 7647 | // | 54.79 | 0.05479 mg |
| 3 | 6017 | 3500 | 69.42 | 0.06942 mg |
| 5 | 5581 | 5394 | 80.54 | 0.08054 mg |
| 6 | 5726 | 5768 | 84.39 | 0.08439 mg |
| 8 | 5778 | 6404 | 89.55 | 0.08955 mg |
| 9 | 5754 | 6545 | 90.43 | 0.09043 mg |

Subsequently 4 mg of SBA-BORT sample were dispersed in 15 ml of the buffer solution. The mixture was left with stirring for the entire duration of the release tests at a temperature of 37° C.

Figure 8:
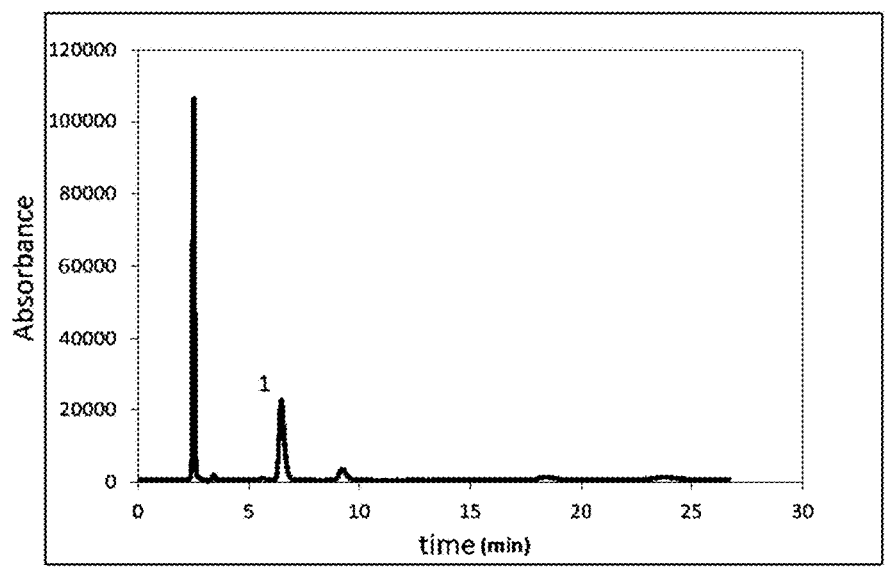
FIG. 8. Chromatogram of Bortezomib in a concentration of 50 ppm in simulated body fluid at pH 7.

Samples of the abovementioned mixture were taken every 30 minutes for HPLC analysis. FIG. 8 shows the chromatogram of Bortezomib in a concentration of 50 ppm in simulated body fluid at pH 7.

Figure 9:
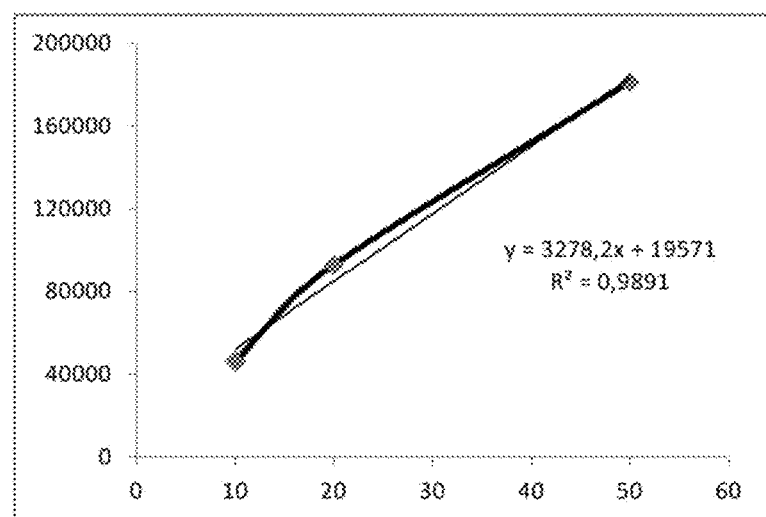
FIG. 9. Calibration line relating to peak 1 of the chromatogram of the solution at pH 7.

The values obtained from the analysis of Bortezomib solutions at different concentrations are shown in Table 4.1 relating to the peak identified by the number 1. The calibration line obtained is shown in FIG. 9.

TABLE 4.1

Values of the area subtended by the peak for the solution at pH 7

| Concentration (ppm) | Peak area (μa) |
|---|---|
| 10 | 46392 |
| 20 | 93083 |
| 50 | 181493 |

Figure 10:
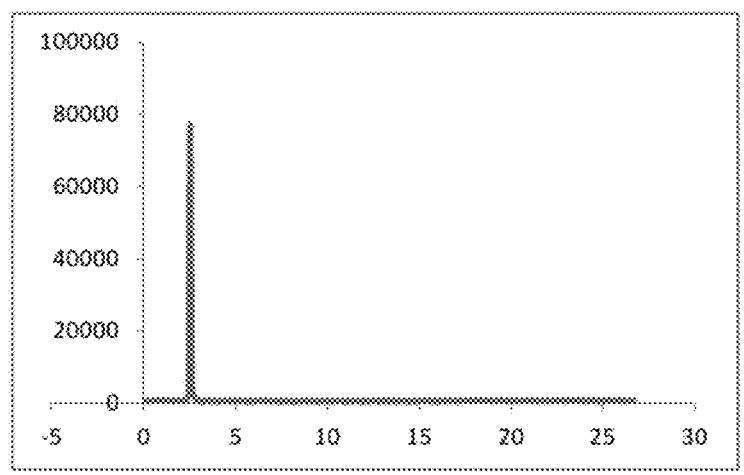
FIG. 10. Chromatogram obtained from the solution buffered to pH 7 in which the Silica (SBA-15)/linker/Bortezomib Conjugate sample was suspended for 0.5 hours.
Figure 11:
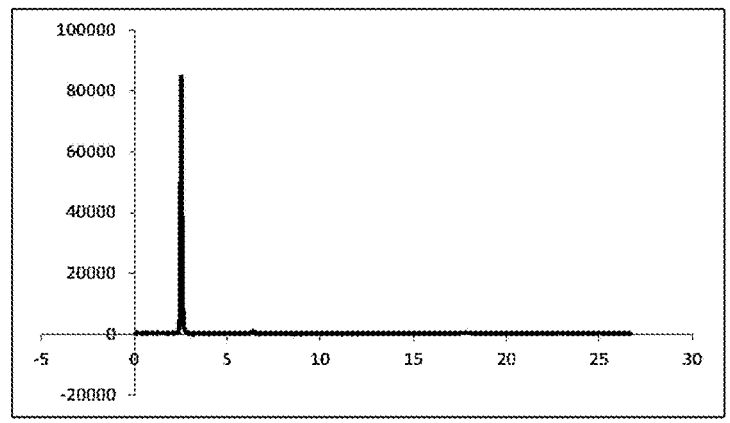
FIG. 11. Chromatogram obtained from the solution buffered to pH 7 in which the Silica (SBA-15)/linker/Bortezomib Conjugate sample was suspended for 9.0 hours.

It will be seen from the two chromatograms shown in FIG. 10 and FIG. 11 that the peak identified by the number 1 in FIG. 8 is almost absent even after 9 hours of suspension in the fluid at pH 7.

In particular, no losses of drug from the Silica (SBA-15)/linker/Bortezomib conjugate system which could be detected by HPLC were observed during approximately the first four hours.

Table 5.1 shows data indicative of the release of Bortezomib at pH 7 as a function of time.

The quantity of Bortezomib released from the Silica (SBA-15)/linker/Bortezomib conjugate system after it had remained in the buffered solution for 9 hours was approximately 50 times less than that detected in the solution buffered at pH 5 over the same period.

Figure 12:
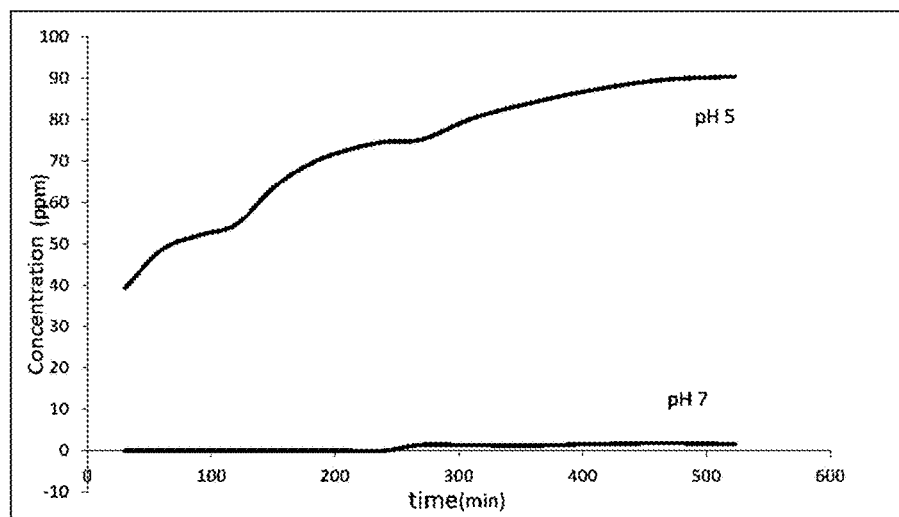
FIG. 12. Release of Bortezomib from simulated body fluids at pH 5 and pH 7 as a function of time.

FIG. 12 shows the progress of the release of Bortezomib at two different pH values: in buffer at pH 5 and pH 7 as a function of time.

From the release data, as demonstrated by FIG. 12.1, it can be concluded that the system is extremely stable within the solution mimicking the blood plasma environment. While the SBA-BORT system remained in solution for up to three hours the technique used did not detect any presence of the drug, after which it remained largely anchored to the mesoporous silica matrix.

The experimental evidence relating to the release of Bortezomib in an acid environment show that significant concentrations of the drug are present in solution even after the SBA-BORT system has been in residence for short times, confirming the lability of the bond of the boronic diester type at slightly acid pH.

TABLE 5.1

Data relating to the release of SBA-BORT at pH = 7 as a function of time

| Time (hours) | Peak area (μa) | BORT concentration found (ppm) | Quantity of BORTEZOMIB released from 4 mg of matrix |
|---|---|---|---|
| 1 | ~0 | ~0 | ~0 |
| 3 | ~0 | ~0 | ~0 |
| 4 | 4693 | 1.43 | 0.00143 mg |
| 6 | 5208 | 1.58 | 0.00158 mg |
| 7 | 5365 | 1.63 | 0.00163 mg |
| 9 | 5839 | 1.78 | 0.00178 mg |

Cell Vitality Experiments

The experiments on cell vitality were therefore performed on systems comprising a matrix based on inorganic oxides having a regular and controlled porosity characterised by the fact that folic acid was selectively coupled to the matrix as the substance responsible for targeting and recognition of the molecule and a Bortezomib prodrug was anchored in the pores.

For this purpose mesoporous silica nanoparticles (MSNs, also referred to as SBA above) were functionalised with folic acid (thus yielding particles referred to as MSN-FOL) or with folic acid and Bortezomib (the latter being referred to as: MSN-FOL/GPS-BTZ) representing the more "complete" product according to the invention, that is to say the drug delivery micro-nanosystem. In this particular case, which was the one tested, the linker was the glycidoxypropyl (GPS) functional group.

Cell update and vitality experiments were performed. The potential toxicity of the nanoparticles was determined by cell vitality experiments which showed that they are not toxic up to a concentration of 3 μg/$10^5$ cells (unreported results), and we therefore continued with this MSNs/number of cells ratio in subsequent experiments.

Figure 13:
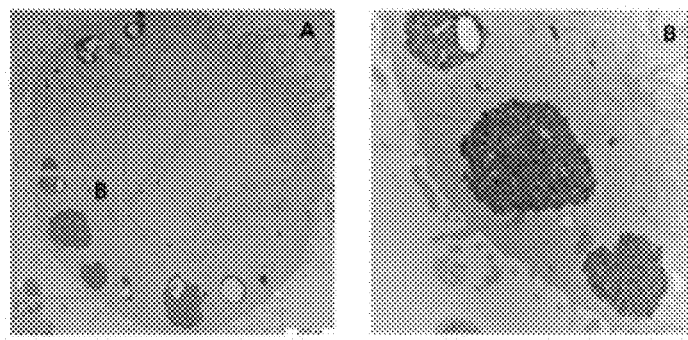
FIGS. 13A and 13B. TEM images illustrating the uptake of MSN-FOL by HeLa cells expressing FR after 1 hour's incubation (see the Materials and Methods section). Image (FIG. 13A) was obtained at a magnification of ×8000, while the area bounded by the square was acquired at a magnification of ×25000 (FIG. 13B).

Observations carried out using an electron microscope (TEM) revealed that the MSN-FOL succeeded in penetrating the HeLa cells expressing high levels of FR even after 1 hour's incubation, being mainly located in endosome formations within the cytoplasm (FIGS. 13A and 13B).

In order to determine whether the nanoparticles could constitute a reliable instrument in targeted therapy, the MSN-FOL was conjugated with Bortezomib using a pH-sensitive system (MSN-FOL/GPS-BTZ). These particles were then engineered in an attempt to obtain an antitumour device which would use the folic acid as a receptor-specific ligand exclusively responsible for recognition of the FR-positive cells, and once receptor endocytosis mediated by the MSNs had occurred a pH-sensitive system capable of releasing the drug only in the acid environment of the endolysosomal cavities.

Figure 14:
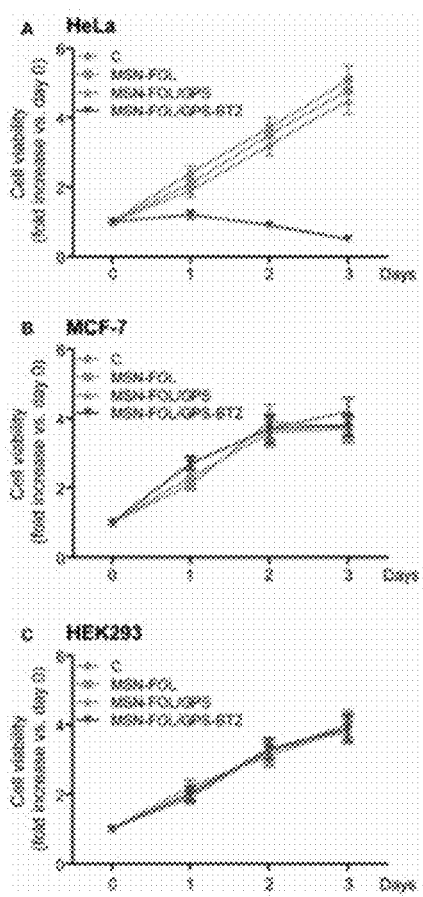
FIGS. 14A to 14C. The MSN-FOL/GPS-BTZ inhibit growth in FR-positive HeLa uterine cervical tumour cells (FIG. 14A) but not in MCF-7mammary carcinoma cells (FIG. 14B) nor in normal HEK293 cells (FIG. 14C), both of which are FR-negative. The cells were treated with MSN-FOL/GPS-BTZ or left untreated (control C). MSN-FOL and MSN- FOL/GPS were used as further negative controls (see Materials and Methods). Cell vitality was assessed after 1, 2 or 3 days of treatment. The values reported represent the mean ± standard deviation of four independent experiments carried out in triplicate for each condition.

The toxicity/efficacy of MSN-FOL/GPS-BTZ was evaluated by cell vitality experiments using the Trypan blue exclusion test (see Materials and Methods). An obvious stop to growth was observed after only 1 day in HeLa (FR-positive) cells treated with MSN-FOL/GPS-BTZ, in comparison with the control. The cytostatic effect was then transmuted into a cytotoxic effect on the second and above all the third day of treatment (FIG. 14A). In confirmation of the fact that the toxicity was exclusively due to the presence of BTZ, the synthesis intermediates MSN-FOL and MSN-FOL/GPS used as a further negative control revealed no significant effects on cell proliferation at any of the times considered (FIG. 14A).

Conversely, MCF-7 breast carcinoma cells and normal HEK293 embryonic kidney cells, both FR-negative lines, showed no inhibition of growth following treatment with MSN-FOL/GPS-BTZ in relation to the control or samples treated with MSN-FOL and MSN-FOL/GPS (FIGS. 14B and 14C) (Morelli C., Maris P, Sisci D, Perrotta E, Brunelli E, Perrotta I, Panno M L, Tagarelli A, Versace C, Casula M F, Testa F, Ando S, Nagy J B, Pasqua L. PEG-templated mesoporous silica nanoparticles exclusively target cancer cells. Nanoscale. 2011 August; 3(8):3198-207).

The data obtained show that our mesoporous silica nanoparticles are a potential vehicle in the field for the controlled release of drugs because they can be selectively recognised and internalised only by tumour cells expressing FR and not by FR-negative cells (e.g. most normal cells). This will allow the drug to be released within lysosomes (pH 4-5) and to act only within the target cells, with a consequent dramatic reduction in the collateral effects due to its non-selective systemic distribution.

Materials and Methods

Cell Lines and Culture Conditions

HeLa human uterine cervical adenocarcinoma cells (American Type Culture Collection, ATCC, USA) and normal HEK293 embryonic kidney cells were cultured in Dulbecco's Modified Eagle's Medium (DMEM), supplemented with 10% of foetal bovine serum (FBS); MCF-7 human breast carcinoma cells (Interlab Cell Line Collection, ICLC, Genoa, Italy) were propagated in DMEM:F12 containing 5% of FBS.

100 IU ml$^{-1}$ of penicillin, 100 µg ml$^{-1}$ of streptomycin and 0.2 mM of L-glutamine were added to both culture media. The media and the reagents were acquired from Gibco® (Thermo Fisher Scientific Inc.).

Transmission Electron Microscopy (TEM)

The cells were seeded in 60 mm diameter cell culture Petri dishes and incubated at 37° C. with MSN-FOL. After 1 hour's incubation the cells were washed and collected in Phosphate Buffer Saline (PBS, Invitrogen, Italy) and centrifuged at 14,000 rpm. The resulting pellet was then immediately fixed in PBS with 3% glutaraldehyde (pH 7.4) for 2 hours, then transferred into 3% osmium tetroxide solution for a further 2 hours, dewatered on an acetone gradient and finally embedded in Araldite (Fluka, Buchs, Switzerland). Ultrathin sections were obtained using a microtome, stratified on a 300 mesh copper grid, contrasted with lead citrate and uranyl acetate and then observed using a "Zeiss EM 900" electron microscope.

Cell Vitality Experiments

The effect of MSNs conjugated with Bortezomib (BTZ) on cell proliferation was evaluated using the Trypan blue exclusion method, a staining agent capable of penetrating through the membranes of damaged or dead cells (which are excluded from the count), but which does not cross the membrane of intact cells (which are instead counted). The cells, at an exponential growth stage, were then inoculated into culture medium in 12 well multiwells, in a quantity of 10$^5$ cells/well, and allowed to grow overnight. On the next day the cells were synchronised in serum-free medium (SFM) in order to obtain a cell population which was at the same stage in the cycle, thus avoiding differences in growth between the cells. After 24 hours 3 µg/10$^5$ MSN-FOL, MSN-FOL/GPS and MSN-FOL/GPS-BTZ cells were added to the cells for 1 hour; the medium was then replaced by a fresh medium to which 5% of FBS had been added and the cells were harvested after 1, 2 or 3 days by trypsinisation and incubated in a 0.5% solution of Trypan blue at ambient temperature for 10 minutes. Cell vitality was determined microscopically by counting the cells which had not taken up the stain (vital cells) using a blood cytometer (Burker, Brand, Germany).

The invention claimed is:
1. A compound of general formula (II)

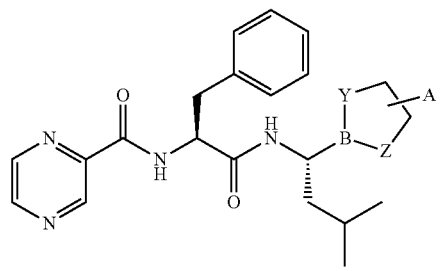

(II)

in which:
Y and Z are selected independently of each other from the group consisting of —NH, —O—, and —S—; and
A is

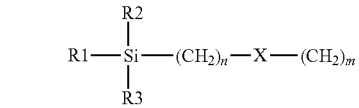

wherein:
R1, R2, and R3 are selected independently of each other from the group consisting of CH$_3$, C$_2$H$_5$, OCH$_3$, OC$_2$H$_5$, OC$_3$H$_7$, OC$_4$H$_9$, and OC$_5$H$_{11}$;
X is a single bond or S, O, or NH; and
n and m are positive integers such that n=0–5 and m=0–3 with n+m>1.

2. The compound of general formula (II) according to claim 1 obtainable by reacting Bortezomib of general formula (I):

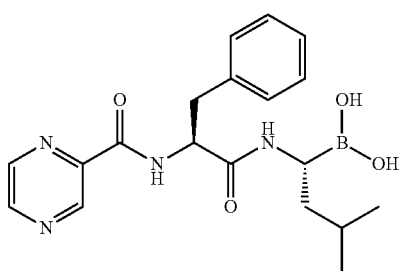

(I)

with a bidentate ligand of general formula (III)

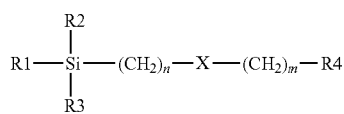

(III)

in which:
R1, R2, and R3 are selected independently of each other from the group consisting of CH$_3$, C$_2$H$_5$, OCH$_3$, OC$_2$H$_5$, OC$_3$H$_7$, OC$_4$H$_9$, and OC$_5$H$_{11}$;
R4 is selected from the group consisting of NH$_2$, SH, epoxide, halogen, CN, thiocyanate, and —CH=CH$_2$;

X is a single bond or S, O, or NH; and n and m are positive integers such that n=0–5 and m=0–3 with n+m>1;

which reacts to form a cyclic boron derivative on the extremity of the ligand bearing R4.

3. The compound of general formula (II) according to claim 2 in which the bidentate ligand of formula (III) is selected from the group consisting of: 3-glycidoxypropyl-trimethoxy-silane;

3-aminopropyltriethoxysilane; 3-aminopropyltrimethoxysilane; 4-aminobutyl-dimethyl methoxysilane; 3-(2-aminoethylamino)propyl-trimethoxysilane(N-[3-(Trimethoxysilyl)propyl]ethylenediannine); 3-[2-(2-aminoethylamino)ethylamino]-propyltrimethoxysilane; $N^1$-(3-trimethoxysilylpropyl)diethylenetriamine; 3-(2-aminoethylamino)propyl-methyldimethoxysilane; 3-mercaptopropyltrimethoxysilane; 3-glycidoxypropyldimethoxymethylsilane; 3-glycidoxypropyldimethylethoxysilane; 3-glycidoxypropyltrimethoxysilane;

allyltriethoxysilane; allyltrimethoxysilane; 3-cyanopropyltriethoxysilane;

chloromethyl(methyl)dimethoxysilane; chloromethyltrimethoxysilane;

chloromethyltriethoxysilane; (3-chloropropyl)dimethoxymethylsilane; (3-chloropropyl)trimethoxysilane; 3-thiocyanatopropyltriethoxysilane; and 3-thiocyanatopropyltrinnethoxysilane.

4. The compound of general formula (II) according to claim 1, which is chemically stable at neutral pH while it decomposes with the release of Bortezomib at slightly acid pH between 4.0 and 5.5.

5. A method of treating, the method comprising administration of said compound of general formula (II) according to claim 1 as an antitumoral prodrug.

6. A drug delivery system comprising the compound of general formula (II) according to claim 1 anchored to a porous inorganic matrix of micro- or nanometric dimensions.

7. The drug delivery system according to claim 6, in which the inorganic matrix comprises inorganic oxides.

8. The drug delivery system according to claim 6, in which the pores of nanometric dimensions are pores having a controlled porosity obtained by an imprinting method or by use of a surfactant.

9. The drug delivery system according to claim 6, in which the inorganic matrix comprises one or more molecules selected from substances responsible for delivery and molecular recognition and molecules acting as markers.

10. The drug delivery system according to claim 9, in which said substances are selected from the group consisting of folic acid, biotin, peptides, antibodies, glycosides, carbohydrates, and proteins.

11. The drug delivery system according to claim 9, in which said marker is a fluorescent marker selected from the group consisting of fluorescein and rhodamine.

12. A pharmaceutical composition comprising the compound of general formula (II) according to claim 1, or a drug delivery system comprising the compound of general formula (II) according to claim 1 anchored to a porous inorganic matrix of micro- or nanometric dimensions, either of which is formulated together with a pharmaceutically acceptable vehicle.

13. The pharmaceutical composition or the drug delivery system according to claim 12, either of which is formulated in combination with other active ingredients or prodrugs.

14. A pharmaceutical composition comprising the compound of general formula (II) according to claim 1, which is formulated for administration via nasal, buccal, oral, intradermal, subcutaneous, intramuscular, intraperitoneal, endovenous, intrathecal, intracranial, parenteral, or intraperitoneal route.

15. A pharmaceutical composition comprising the compound of general formula (II) according to claim 1, which is formulated as an injectable formulation wherein said injectable formulation is a sterile aqueous solution or dispersion, or as a sterile powder for preparation of an extemporaneous dispersion.

16. A kit comprising the pharmaceutical composition or the drug delivery system according to claim 12, either of which is prepared in predetermined doses for sole or simultaneous, sequential or retarded administration of other active ingredients or prodrugs.

17. A method for treating, improving the clinical condition of, or alleviating collateral affects in an individual suffering from cervical cancer; comprising administration of a pharmaceutical composition comprising the compound of general formula (II) according to claim 1 to the individual.

18. A method for treating, improving the clinical condition of, or alleviating collateral affects in an individual suffering from cervical cancer; comprising administration of the kit according to claim 16 to the individual.

19. A method for treating, improving the clinical condition of, or alleviating collateral affects in an individual suffering from a tumour; comprising administration of the drug delivery system according to claim 9 to the individual, wherein the substance is responsible for molecular recognition by the tumour such that it is targeted for delivery of Bortezomib.

20. A method for treating, improving the clinical condition of, or alleviating collateral affects in an individual suffering from a tumour; comprising administration of the drug delivery system according to claim 10 to the individual.

* * * * *